(12) United States Patent
Hechler et al.

(10) Patent No.: US 7,326,802 B2
(45) Date of Patent: Feb. 5, 2008

(54) PREPARATION OF AT LEAST ONE PARTIAL OXIDATION AND/OR AMMOXIDATION PRODUCT OF PROPYLENE

(75) Inventors: Claus Hechler, Ludwigshafen (DE);
Götz-Peter Schindler, Mannheim (DE);
Jochen Petzoldt, Mannheim (DE);
Christoph Adami, Weinheim (DE);
Otto Machhammer, Mannheim (DE);
Klaus Joachim Müller-Engel,
Stutensee (DE); Hans Martan,
Frankenthal (DE)

(73) Assignee: BASF Aktiengesellschaft,
Ludwigshafen (DE)

( * ) Notice: Subject to any disclaimer, the term of this patent is extended or adjusted under 35 U.S.C. 154(b) by 428 days.

(21) Appl. No.: 10/465,656

(22) Filed: Jun. 20, 2003

(65) Prior Publication Data

US 2004/0063988 A1    Apr. 1, 2004

(30) Foreign Application Priority Data

Sep. 27, 2002   (DE) ................. 102 45 585
Oct. 1, 2002    (DE) ................. 102 46 119

(51) Int. Cl.
*C07C 253/00*   (2006.01)
*C07C 491/00*   (2006.01)

(52) U.S. Cl. ..................... 558/320; 558/466
(58) Field of Classification Search ............. 549/518, 549/523, 533, 534, 536; 558/320, 466
See application file for complete search history.

(56) References Cited

U.S. PATENT DOCUMENTS

| | | | | |
|---|---|---|---|---|
| 482,771 A * | 9/1892 | Hazbun | ....... | 118/502 |
| 3,798,283 A | 3/1974 | Bitar et al. | ....... | 585/656 |
| 3,865,873 A | 2/1975 | Oda et al. | ....... | 562/532 |
| 4,066,704 A | 1/1978 | Harris et al. | ....... | 568/475 |
| 4,077,912 A | 3/1978 | Dolhyj et al. | ....... | 502/178 |
| 4,658,074 A * | 4/1987 | Bajars et al. | ....... | 585/380 |
| 5,268,497 A | 12/1993 | Ramachandran | ....... | 558/320 |
| 5,705,684 A | 1/1998 | Hefner et al. | ....... | 562/545 |
| 2003/0181762 A1 | 9/2003 | Machhammer et al. | ..... | 562/545 |
| 2003/0187298 A1 | 10/2003 | Borgmeier et al. | ....... | 562/546 |
| 2003/0187299 A1 | 10/2003 | Machhammer et al. | ..... | 562/547 |

FOREIGN PATENT DOCUMENTS

| | | |
|---|---|---|
| DE | 2 058 054 | 6/1971 |
| DE | 2 251 364 | 5/1973 |
| DE | 2 351 151 | 4/1974 |
| DE | 35 21 458 | 12/1985 |
| DE | 100 51 419 | 4/2002 |
| DE | 101 19 933 | 10/2002 |
| DE | 101 22 029 | 11/2002 |
| DE | 101 31 297 | 1/2003 |
| EP | 0 117 146 | 8/1984 |
| EP | 0 293 224 | 11/1988 |
| EP | 0 372 972 | 6/1990 |
| EP | 0 529 853 | 3/1993 |
| EP | 0 608 838 | 8/1994 |
| EP | 0 731 077 | 9/1996 |
| EP | 1 192 987 | 4/2002 |
| EP | 0 938 463 | 6/2002 |
| GB | 2 160 543 | 12/1985 |
| WO | WO 00/20404 | 4/2000 |
| WO | WO 01/96270 | 12/2001 |
| WO | WO 01/96271 | 12/2001 |

OTHER PUBLICATIONS

Oshihara, Topics in Catalysis, vol. 15(2-4), pp. 153-160, 2001.*

* cited by examiner

*Primary Examiner*—D. Margaret Seaman
(74) *Attorney, Agent, or Firm*—Oblon, Spivak, McClelland, Maier & Neustadt, P.C.

(57) ABSTRACT

In a process for preparing at least one partial oxidation and/or ammoxidation product of propylene, the propylene is obtained from crude propane by dehydrogenating and subjected in the presence of unconverted propane as a constituent of a gas mixture 2 which comprises a total $C_4$-hydrocarbon content of $\leq 3\%$ by volume to a heterogeneously catalyzed gas phase partial oxidation and/or partial gas phase ammoxidation.

51 Claims, No Drawings

PREPARATION OF AT LEAST ONE PARTIAL OXIDATION AND/OR AMMOXIDATION PRODUCT OF PROPYLENE

The present invention relates to a process for preparing at least one partial oxidation and/or ammoxidation product of propylene by a) in a first step, subjecting crude propane in the presence of and/or with the exclusion of oxygen to a homogeneously and/or a heterogeneously catalyzed dehydrogenation and/or oxydehydrogenation to obtain a propane- and propylene-containing gas mixture 1, and b) optionally removing and/or converting to other compounds a portion of the constituents other than propane and propylene contained in the gas mixture 1 formed in the first step to obtain, from the gas mixture 1, a gas mixture 1' comprising propane and propylene and also compounds other than oxygen, propane and propylene, and, in at least one further step c) subjecting gas mixture 1 and/or gas mixture 1' as a constituent of a gas mixture 2 to a heterogeneously catalyzed gas phase partial oxidation and/or partial gas phase ammoxidation of propylene contained in gas mixture 1 and/or gas mixture 1'.

In this document, crude propane refers to a propane-containing gas which, in addition to propane and, if present, propylene, comprises at least one chemical compound, frequently at least two or three and in many cases at least four or five chemical compounds, other than propane and propylene. The latter is the case when such chemical compounds can be detected in crude propane by chromatography, e.g. gas chromatography.

In this document, oxydehydrogenation of propane refers to a dehydrogenation which is forced by oxygen present and in which no free hydrogen is formed as an intermediate or can be detected. In contrast to the conventional dehydrogenation which proceeds endothermically, the heat of reaction of oxydehydrogenation is exothermic. The oxydehydrogenation of propane may be carried out under the action of elevated temperature, either homogeneously (i.e. without the presence of, or example, a solid catalyst; cf., for example, U.S. Pat. No. 3,798,283) or else heterogeneously catalyzed (for example over solid catalysts; cf. DE-A 2058054 and DE-A 19530494).

The same applies substantially for the conventional dehydrogenation in which the dehydrogenation step is effected without active participation of oxygen (cf., for example, EP-A 731 077 and WO 01/96270). In other words, the primary by-product formed in this case is hydrogen and not water as in the case or oxydehydrogenation.

In this document, a complete oxidation of propylene refers to the total amount of carbon present in the propylene being converted to oxides of carbon ($CO$, $CO_2$). All different reactions of propylene with the reactive participation of molecular oxygen will be encompassed in this document by the term partial oxidation. The additional reactive participation of ammonia characterizes the ammoxidation.

The partial oxidation and/or ammoxidation products of propylene preferred in this document are acrolein, acrylic acid, propylene oxide and acrylonitrile.

Partial oxidation and/or ammoxidation products of propylene are important intermediates, for example for preparing polymers.

The implementation of such partial oxidations and/or ammoxidations (selecting the ammonia content to be controlled in a manner known per se in the reaction gas mixture allows the reaction to be configured substantially exclusively as a partial oxidation, or exclusively as a partial ammoxidation, or as a superimposition of both reactions) is known per se. These are heterogeneously catalyzed gas phase reactions over solid, generally oxidic, catalysts.

DE-A 2 351 151 (example of the conversion of propylene to acrolein and/or acrylic acid and also of propylene to acrylonitrile) and EP-A 372 972 (example of the conversion of propylene to propylene oxide) are cited by way of example.

The oxidizing agent used is normally molecular oxygen which may be added to the reaction gas mixture in pure form or in a mixture with gases which behave substantially inertly with regard to the partial oxidation/ammoxidation (for example as air). Frequently, the reactants in the reaction gas mixture are also diluted for reasons of heat removal and for reasons of safe reaction control by at least one inert gas (e.g. $N_2$, $H_2O$, $CO$, $CO_2$, saturated, for example $C_1$-$C_5$, hydrocarbons (for example according to DE-A 1924431 and EP-A 293224), He and/or Ar, etc.). One inert diluent gas whose use is recommended by DE-B 2251364 is butane. The ammoxidation differs, as already mentioned, by additional presence of ammonia.

The starting propylene used on the industrial scale, in contrast to laboratory and pilot plant experiments, is not chemically pure, but rather crude propylene which has impurities but does, however, have a comparatively high purity (e.g. "polymer grade" or "chemical grade"; cf. DE-A 10131297).

The provision of such comparatively pure crude propylene is relatively inconvenient and costly. It normally starts from crude paraffinic hydrocarbons and generally comprises at least one purification stage in which unconverted paraffinic hydrocarbon is removed from propylene formed by means of physical processes (cf., for example, DE-A 3 521 458). Typically, the at least one purification stage also encompasses a separation of olefins other than propylene and also of by-products other than propylene, including the secondary components already present in the crude paraffinic hydrocarbon.

The abovementioned removals are generally capital-intensive and, as a consequence of the similarity of olefinic/paraffinic hydrocarbons, very energy-intensive. They are therefore customarily only applied in an integrated system with refinery crackers and steam crackers and only pay off because the vast majority of the crude propylene obtained in this way is on the one hand required in large amounts for subsequent polymerization (e.g. preparation of polypropylene) (economy of scale) and, on the other hand, experiences high addition of value in these polymerizations.

The proportion of these crude propylenes flowing into partial oxidations and/or ammoxidations is rather of minor importance and is an inconsequential secondary consumption stream, which is why crude propylene obtained in this way still has an acceptable raw material price for partial oxidations and/or ammoxidations.

This raw material price could only be noticeably reduced if at least some of the separations mentioned or all of them could be dispensed with.

A solution to the problem proposed by EP-B 938463 is, in a first step, to partially dehydrogenate crude propane, for example, in the presence of oxygen with heterogeneous catalysis to obtain a first gas mixture comprising propylene and propane which is subjected as such, i.e. without intermediate treatment, as a constituent of a second gas mixture to a heterogeneously catalyzed gas phase partial oxidation of propylene contained in the first gas mixture to acrolein and/or acrylic acid.

On the question of purity of the crude propane to be used, EP-B 938463 sets out in column 3, line 40 ff., inter alia: "The purity of the starting material alkane is not particularly limited". "Further, the starting material alkane may be a mixture of various alkanes. Typically the feed will comprise at least 30 mole percent, preferably at least 50 mole percent and more preferably at least 80 mole percent propane. The source of the alkane, e.g. propane feed, for use in the process of the present invention is not critical."

Furthermore, EP-B 938463 teaches in column 3, line 17 ff.: "Hence, after recovery of the acrolein, the noncondensed gases containing propane may be recycled without significant, additional purification steps."

The teaching of EP-A 117146 corresponds substantially to EP-B 938463, apart from EP-A 117146 recommending the implementation of the heterogeneously catalyzed dehydrogenation of propane with the exclusion of oxygen.

With regard to the abovementioned recycle stream, EP-A 117146 further teaches on page 11, lines 14ff.: "Since the light and heavy hydrocarbon by-products, such as methane, ethane, ethylene, butane, and butenes boil at temperatures significantly different from those of acrolein or the $C_3$ hydrocarbons, they may be separated by distillation. Alternatively, streams containing the by-products in concentrated amounts may be purged." The possibility of such a purge stream of recycle gas is also seen by EP-B 938463 in column 11, line 10.

The necessity of removing the abovementioned secondary components in advance of the partial oxidation and/or ammoxidation is seen by neither document.

The teaching of WO 01/96270 follows the teaching given in EP-B 938463 and in EP-A 117 146. For instance, it sets out on page 4, line 10 ff.: "Of course, the feed gas mixture or oxidation stage B in the novel procedure may contain, in addition to the abovementioned components, also other components, e.g. CO, $CO_2$, $H_2O$, noble gases such as He and/or Ar, hydrogen, methane, ethylene, butanes, butenes, butynes, pentanes, propyne, allenes and/or acrolein."

With regard to the crude propane to be used for the dehydrogenation step, WO 01/96270 teaches on page 15, lines 26 ff.: "According to the invention, it is essential that the propane used in stage A is not pure propane. Rather, the propane used may contain up to 50% by volume of other gases, such as ethane, methane, ethylene, butanes, butenes, propyne, acetylene, $H_2S$, $SO_2$, pentanes, etc."

WO 01/96270 also recommends removing at least a portion of the hydrogen contained in the propane- and propylene-containing first gas mixture formed in the dehydrogenation step and, in the course of this removal, optionally also removing other, optionally substantially all constituents other than propane and propylene, from the first gas mixture before it is used further for the partial oxidation of the propylene contained therein, and EP-B 731077 even regards as particularly preferred a quantitative removal of all constituents other than propane, propylene and, if present, molecular oxygen from such a first gas mixture before it is used further. However, on the one hand, a separating process to be used for this purpose reduces the economic viability of the overall process and, on the other hand, some of the processes recommended in the abovementioned documents prove to be ill-suited to such a quantitative removal. The latter applies, for example, to the absorption/desorption process recommended in WO 01/96270 on page 16 at the bottom, which, on closer examination, proves to be ill-suited in order to separate, for example, $C_4$-hydrocarbons from $C_3$-hydrocarbons.

The necessity when changing the raw material from crude propylene to crude propane of removing certain secondary components after the dehydrogenation and/or oxydehydrogenation step or even before this step in order to reduce the formation of by-products alongside the formation of the desired target product in the at least one oxidation and/or ammoxidation step is not seen by the cited prior art. Although it is aware of the changing by-product formation with the change of raw material (according to WO 01/96270, for example, the presence of propane in the partial oxidation results in increased propionaldehyde and/or propionic acid formation; however, the advantage of not removing the propane from the propylene formed in the dehydrogenation is valued more highly), it does not regard this as particularly critical insofar as a preceding removal is generally more costly and inconvenient than the separation of target product and by-product. This is even against the background that a target product removal from secondary components formed has in any case to be carried out.

This opinion is quite obviously shared by those who, like EP-A 1192987 or DE-A 10122027, or EP-A 608838, or EP-A 529853, or DE-A 10051419, or DE-A 10119933, recommend carrying out the process defined at the outset of this document in a single reaction zone (usually it is carried out in at least two reaction zones) over a catalyst charge whose active oxide composition is at least one multimetal oxide which comprises the elements Mo, V and Te and/or Sb. The basis of this procedure is that the relevant active oxide composition is able on the one hand to catalyze the oxydehydrogenation of propane to propylene (cf., for example, EP-B 938463, column 4, line 37 ff.) and on the other hand the partial oxidation and/or ammoxidation of propylene. It will be appreciated that the gas mixture 1 in such a procedure is used as such for the subsequent at least one partial oxidation and/or ammoxidation step.

Nevertheless, EP-A 1192987, for example, recommends on page 9, line 26 ff.: "Similarly, there is no limitation on the source of the alkane. It may be purchased, per se, or in admixture with an alkene and/or other impurities. Moreover, the alkane, regardless of source, and the alkene, regardless of source, may be blended as desired." In complete contradiction, DE-A 10122027 teaches on page 3, lines 35/36: "The propane to be used for the novel process does not have to meet any particularly high requirements with regard to its purity."

WO 0196271 likewise regards crude propane of differing purity as usable.

A disadvantage of the above prior art recommendations is that they do not analyze which of any constituents already present in inexpensive crude propane or which chemical compounds forming in the course of the first step from such constituents and then being present in the first gas mixture (said compounds only being present in traces, if at all, in the crude propylenes normally used, so that their negative effects remain hitherto unnoticed) act as catalyst poisons with regard to the subsequent heterogenetously catalyzed partial oxidation and/or ammoxidation by reducing the activity and/or selectivity with respect to the desired partial oxidation and/or ammoxidation of propylene.

As a result of detailed and careful investigations, it has now been found that $C_4$-hydrocarbons (chemical compounds which consist of four carbon atoms and hydrogen) generally form such catalyst poisons, and among these in particular the group of olefinic representatives (butene-1, trans-butene-2, cis-butene-2 and isobutene), and among these in turn especially butene-1. However, the saturated representatives (n-butane and isobutane) and the other unsaturated representatives also have adverse effects.

However, it is precisely $C_4$-hydrocarbons (e.g. n-butane, isobutane, trans-butene-2, cis-butene-2, isobutene, butadiene-1,3, butadiene-1,2, butyne-1 and/or butyne-2) which form ubiquitous companions of propane and are therefore typically present in significant amounts in inexpensive crude propanes. This statement applies to a very particular extent to the saturated $C_4$-hydrocarbons, from which, however, under the conditions of a partial dehydrogenation and/or oxydehydrogenation of propane, the olefinic $C_4$-hydrocarbons are at least partly formed, in particular the particularly troublesome butene-1.

It is an object of the present invention to provide a process as described at the outset for preparing at least one partial oxidation and/or ammoxidation product of propylene which, in contrast to prior art processes, takes account of the abovementioned facts.

We have found that this object is achieved by a process for preparing at least one partial oxidation and/or ammoxidation product of propylene by a) in a first step, subjecting crude propane in the presence of and/or with the exclusion of oxygen to a homogeneously and/or a heterogeneously catalyzed dehydrogenation and/or oxydehydrogenation to obtain a propane- and propylene-containing gas mixture 1 and b) optionally removing and/or converting to other compounds a portion of the constituents other than propane and propylene contained in the gas mixture 1 formed in the first step to obtain, from the gas mixture 1, a gas mixture 1' comprising propane and propylene and also compounds other than oxygen, propane and propylene, and, in at least one further step c) subjecting gas mixture 1 and/or gas mixture 1' as a constituent of a gas mixture 2 to a heterogeneously catalyzed gas phase partial oxidation and/or partial gas phase ammoxidation of propylene contained in gas mixture 1 and/or gas mixture 1', wherein
the total content of $C_4$-hydrocarbons of gas mixture 2 is ≦3% by volume.

The amount of the constituents other than propane and propylene which are removed from gas mixture 1 and/or converted to other compounds on the route to gas mixture 1' may, based on the amount of these constituents present in gas mixture 1 in the process according to the invention, be up to 5% by weight, or up to 10% by weight, or up to 20% by weight, or up to 30 or 40% by weight, or up to 60% by weight, or up to 70 or 80% by weight, or up to 85 or 90% by weight, or up to 94% by weight, or up to 96 or 98% by weight, or up to 99% by weight or more.

According to the invention, the total content of $C_4$-hydrocarbons of gas mixture 2 is ≦2.5% by volume, better ≦2.0% by volume, still better ≦1.5% by volume, or ≦1.0% by volume, or ≦0.50% by volume and most preferably ≦0.30% by volume, or ≦0.10% by volume.

In the case of gas mixtures 2 which no longer contain any $C_4$-hydrocarbons at all, it will be appreciated that their negative effect no longer appears at all. However, for the purposes of an overall economic appraisal, it may be justifiable to accept a certain detrimental effect of the $C_4$-hydrocarbons in gas mixture 2, and to leave their overall content in gas mixture 2 at values of ≧0.05% by volume, or ≧0.07% by volume, or ≧0.09% by volume, or ≧0.1% by volume or, in extreme cases, ≧0.2% by volume.

According to the invention, concurrently with the abovementioned overall contents of $C_4$-hydrocarbons, preference is given to the butene-1 content of gas mixture 2 being ≦1% by volume, or ≦0.9% by volume, or ≦0.75% by volume, or ≦0.6% by volume, or ≦0.5% by volume, or ≦0.4% by volume, more preferably ≦0.3% by volume, even more preferably ≦0.2% by volume and even better ≦0.1% by volume or ≦0.05% by volume, or ≦0.03% by volume or ≦0.01% by volume. In the case of gas mixtures 2 which no longer contain any butene-1 at all, it will be appreciated that their negative effect no longer appears at all. However, for the purposes of an overall economic appraisal, it may be justifiable to accept a certain detrimental effect of the butene-1 in gas mixture 2, and to leave its content in gas mixture 2 at values of ≧0.001% by volume, or ≧0.003% by volume, or ≧0.006% by volume, or, in extreme cases, ≧0.009% by volume.

For the purposes of the present invention, preference is given to the abovementioned limiting values applying, concurrently with the total contents of $C_4$-hydrocarbons mentioned before, not only to the amount of butene-1 contained in gas mixture 2, but also, independently thereof, concurrently to every other possible representative among the butenes (i.e. to trans-butene-2, to cis-butene-2 and to isobutene), and very particular preference is given to the abovementioned limiting values also applying concurrently to the total amount of butenes in gas mixture 2. In other words, examples of gas mixtures 2 suitable according to the invention are those in which:

total content of $C_4$-hydrocarbons ≦3% by volume and total content of butenes ≦1% by volume; or
total content of $C_4$-hydrocarbons ≦2.5% by volume and total content of butenes ≦1% by volume; or
total content of $C_4$-hydrocarbons ≦2.0% by volume and total content of butenes ≦1% by volume; or
total content of $C_4$-hydrocarbons ≦1.5% by volume and total content of butenes ≦1% by volume; or
total content of $C_4$-hydrocarbons ≦1.0% by volume and total content of butenes ≦0.75% by volume; or
total content of $C_4$-hydrocarbons ≦1.0% by volume and total content of butenes ≦0.50% by volume; or
total content of $C_4$-hydrocarbons ≦0.5% by volume and total content of butenes ≦0.30% by volume; or
total content of $C_4$-hydrocarbons ≦0.3% by volume and total content of butenes ≦0.1% by volume; etc.

In order to keep to the abovementioned limiting values, the process according to the invention offers substantially two possibilities, of which either only one or both may be applied.

One possibility is to start from crude propane which either no longer contains any $C_4$-hydrocarbons at all, or contains $C_4$-hydrocarbons only in such amounts that fulfill the limits to be observed according to the invention for the total contents of
$C_4$-hydrocarbons, total butenes and also butene-1 in gas mixture 2. Which content of which of the possible $C_4$-hydrocarbons in the crude propane is compatible with the process according to the invention depends, among other factors, upon the specific boundary conditions used for the step of the process and may be determined by those skilled in the art in a few preliminary experiments, adapted in each case to the specific boundary conditions.

Any removal of $C_4$-hydrocarbons from commercially obtained crude propane which is necessary may be carried out in a manner known per se, for example rectificatively. It will be appreciated that all other separating processes, e.g. adsorption/desorption (e.g. pressure swing adsorption), extraction and/or absorption/desorption additionally come into consideration.

Supplementarily and/or alternatively, it is possible to remove $C_4$-hydrocarbons in general and butene-1 or butenes in particular from gas mixture 1 in advance of its further use according to the invention as gas mixture 1' to such an extent that their levels attain the maximum limits to be observed according to the invention, or are below them. This measure is appropriate, for example, when the troublesome $C_4$-hydrocarbons are formed, for example from propane, only in the course of the oxydehydrogenation or dehydrogenation step, for example by disproportionation and/or metathesis. One factor which increases the probability thereof is the use of the partial cycle gas method of DE-A 10211275 in the first step of the process according to the invention (in the case of a catalytic dehydrogenation). Examples of useful separating processes include the combination of absorption and desorption or stripping (preferably as a pressure absorption), described in DE-A 10131297, pressure swing adsorption, rectification and/or extractive processes. In the case of stripping, care has to be taken that no $C_4$-hydrocarbons are introduced via the stripping gas used.

When the propane and propene (for example absorptively removed from the product gas mixture of a catalytic dehydrogenation) accumulated in the absorbent are stripped free of the absorbent by means of air, the combination may be one of the process combinations according to the invention in which the gas mixture 1' obtained by stripping free of the absorbent may, when the amount of stripping gas is selected appropriately, be used immediately for the partial gas phase partial oxidation and/or the partial gas phase ammoxidation and thus be identical to gas mixture 2. In this case, the content of components other than propane, propene and oxygen in gas mixture 1' will generally be from 35 to 55% by volume. In the case of the preparation of acrolein and/or acrylic acid according to the invention, preference is given to such a procedure.

It will be appreciated that the removals of $C_4$-hydrocarbons discussed may also be accompanied by removal of other constituents other than propane and propylene. Proportions of propane and/or propylene may of course each also be removed at the same time.

According to the invention, the separating processes discussed will advantageously be targeted to a removal of $C_4$-hydrocarbons, in order to limit the separation costs and inconvenience required overall and therefore the detraction from the economic viability.

In other words, a gas mixture 1' in the process according to the invention will normally still contain at least $\geq 0.1\%$ by volume, frequently $\geq 0.2\%$ by volume, or $\geq 0.3\%$ by volume or $\geq 0.4\%$ by volume, or $\geq 0.5\%$ by volume, in many cases $\geq 0.6\%$ by volume, or $>0.8\%$ by volume, or $\geq 1\%$ by volume, often $\geq 2\%$ by volume, or $\geq 3\%$ by volume or $\geq 5\%$ by volume, entirely typically $\geq 10\%$ by volume, or $\geq 15\%$ by volume or $\geq 20\%$ by volume, or $\geq 25\%$ by volume, or $>30\%$ by volume, or $\geq 35\%$ by volume of constituents other than propane and propylene and also oxygen.

However, in the general case, the proportion of constituents other than propane and propylene and also oxygen in gas mixture 1' in the process according to the invention will be $\leq 80\%$ by volume, or $\leq 70\%$ by volume, or $\leq 60\%$ by volume, or $\leq 50\%$ by volume, or $\leq 40\%$ by volume.

As already stated, it is advantageous according to the invention when the removals previously discussed are carried out in such a way that gas mixture 2 has not only the total contents of $C_4$-hydrocarbons suitable according to the invention but also concurrently a butene-1 content which is $\leq 1\%$ by volume, or $\leq 0.9\%$ by volume etc.

In other words, the targets of the procedure according to the invention are achieved in particular when, for gas mixture 2, at least one limit set according to the invention for the total content of $C_4$-hydrocarbons and, concurrently, one limit set in this document for the butene-1 content are fulfilled.

In other words, examples of gas mixtures 2 suitable according to the invention are those which concurrently fulfill the following conditions:

total content of $C_4$-hydrocarbons $\leq 3\%$ by volume and butene-1 content $\leq 1\%$ by volume; or
total content of $C_4$-hydrocarbons $\leq 2\%$ by volume and butene-1 content $\leq 1\%$ by volume; or
total content of $C_4$-hydrocarbons $\leq 3\%$ by volume and butene-1 content $\leq 0.5\%$ by volume; or
total content of $C_4$-hydrocarbons $\leq 2\%$ by volume and butene-1 content $\leq 0.5\%$ by volume; or
total content of $C_4$-hydrocarbons $\leq 3\%$ by volume and butene-1 content $\leq 0.75\%$ by volume; or
total content of $C_4$-hydrocarbons $\leq 2\%$ by volume and butene-1 content $\leq 0.75\%$ by volume; or
total content of $C_4$-hydrocarbons $\leq 3\%$ by volume and butene-1 content $\leq 0.4\%$ by volume; or
total content of $C_4$-hydrocarbons $\leq 2\%$ by volume and butene-1 content $\leq 0.4\%$ by volume; or
total content of $C_4$-hydrocarbons $\leq 1\%$ by volume and butene-1 content $\leq 0.4\%$ by volume; or
total content of $C_4$-hydrocarbons $\leq 3\%$ by volume and butene-1 content $\leq 0.3\%$ by volume; or
total content of $C_4$-hydrocarbons $\leq 2\%$ by volume and butene-1 content $\leq 0.3\%$ by volume; or
total content of $C_4$-hydrocarbons $\leq 1\%$ by volume and butene-1 content $\leq 0.3\%$ by volume; etc.

Particularly advantageous gas mixtures 2 for the process according to the invention are those in which at least one limit set in this document for the total content of butenes in gas mixture 2 is concurrently fulfilled.

In other words, gas mixtures 2 suitable according to the invention are in particular those in which the following conditions are concurrently fulfilled:

total content of $C_4$-hydrocarbons $\leq 3\%$ by volume and total content of butenes $\leq 1\%$ by volume and butene-1 content $\leq 1\%$ by volume; or
total content of $C_4$-hydrocarbons $\leq 3\%$ by volume and total content of butenes $\leq 1\%$ by volume and butene-i content $\leq 0.75\%$ by volume; or
total content of $C_4$-hydrocarbons $\leq 3\%$ by volume and total content of butenes $\leq 1\%$ by volume and butene-1 content $\leq 0.5\%$ by volume; or
total content of $C_4$-hydrocarbons $\leq 3\%$ by volume and total content of butenes $\leq 1\%$ by volume and butene-1 content $\leq 0.3\%$ by volume; or
total content of $C_4$-hydrocarbons $\leq 3\%$ by volume and total content of butenes $\leq 0.75\%$ by volume and butene-1 content $\leq 0.5\%$ by volume; or
total content of $C_4$-hydrocarbons $\leq 3\%$ by volume and total content of butenes $\leq 0.5\%$ by volume and butene-1 content $\leq 0.5\%$ by volume; or
total content of $C_4$-hydrocarbons $\leq 2\%$ by volume and total content of butenes $\leq 0.5\%$ by volume and butene-1 content $\leq 0.5\%$ by volume; etc.

According to the invention, particularly advantageous processes are those in which not only the abovementioned combinations of total content of $C_4$-hydrocarbons and total content of butenes and also optionally butene-1 content in gas mixture 2 are fulfilled, but also, at the same time, a gas mixture 1' is used which still contains at least ≧0.1% by volume, or ≧0.2% by volume, or ≧0.3% by volume, or ≧0.4% by volume, or ≧0.5% by volume, or ≧0.6% by volume, or ≧0.8% by volume, or ≧1% by volume, or ≧2% by volume, or ≧3% by volume, or ≧5% by volume, or ≧10% by volume, or ≧15% by volume, or ≧20% by volume, or ≧25% by volume, or ≧30% by volume, (but usually ≦80% by volume, or ≦70% by volume, or ≦60% by volume, or ≦50% by volume) of constituents other than propane and propylene and also oxygen.

The studies carried out for the purposes of this invention further showed that, for the purposes of avoiding undesired complete combustion of propylene in the partial oxidation and/or ammoxidation, it is generally advantageous when the propane content in gas mixture 2 is comparatively limited. According to the invention, preference is given to the propane content in gas mixture 2 being ≦60% by volume, or ≦50% by volume. Particularly advantageous propane contents in gas mixture 2 are from 20 to 40% by volume, for example about 30% by volume.

When any ammonia content to be used for nitrile generation is not taken into consideration (i.e. is also not taken into account in the basis for the percentages by volume), gas mixtures 2 suitable for the process according to the invention are generally those which, on the one hand, fulfill the limits according to the invention with regard to their total $C_4$-hydrocarbon content, preferably additionally with regard to their butene-1 content and more preferably additionally to their total butene content, and, on the other hand, have the following contents:

from 7 to 15% by volume of $O_2$
from 5 to 10% by volume of propylene,
from 15 to 40% by volume of propane, frequently from 25 to 35% by volume,
from 25 to 60% by volume of nitrogen, frequently from 40 to 60% by volume,
a sum of from 1 to 5% by volume of CO, $CO_2$ and $H_2O$ and from 0 to 5% by volume of other constituents.

The above statement applies in particular when gas mixture 2 for a heterogeneously catalyzed partial oxidation of the propylene contained in gas mixture 2 is used for preparing acrolein and/or acrylic acid.

Otherwise, useful gas mixtures 2 for all heterogeneously catalyzed partial oxidations and/or ammoxidations of propylene encompassed by the process according to the invention are in particular those which, again disregarding any $NH_3$ content present for nitrile formation (also in the reference basis), lie within the following composition pattern:

$H_2O$≦60% by volume, usually ≦20% by volume, generally from 0 to 5% by volume;
$N_2$≦80% by volume, usually ≦70% by volume, generally from 40 to 60% by volume;
$O_2$ up to 20% by volume, usually from 2 to 20% by volume, generally from 5 to 15% by volume;
CO≦2% by volume, usually ≦1% by volume, generally from 0 to 0.5% by volume;
$CO_2$≦5% by volume, usually ≦3% by volume, generally from 0 to 2% by volume;
ethane ≦10% by volume, usually ≦5% by volume, generally from 0 to 2% by volume;
ethylene ≦5% by volume, usually ≦2% by volume, generally from 0 to 0.5% by volume;
methane ≦5% by volume, usually ≦2% by volume, generally from 0 to 0.2% by volume;
propane >0, ≦50% by volume, usually from 10 to 50% by volume, generally from 20 to 40% by volume;
cyclopropane ≦0.1% by volume, usually ≦0.05% by volume, generally from 0 to 150 ppm by volume;
propyne ≦0.1% by volume, usually ≦0.05% by volume, generally from 0 to 150 ppm by volume;
propadiene ≦0.1% by volume, usually ≦0.05% by volume, generally from 0 to 150 ppm by volume;
propylene >0, ≦30% by volume, usually ≧2, ≦20% by volume, generally from 5 to 10% by volume;
$H_2$≦30% by volume, usually ≦20% by volume, generally from 0 to 10% by volume;
isobutane ≦3% by volume, preferably ≦2% by volume, frequently from 0.1 to 1% by volume;
n-butane ≦3% by volume, preferably ≦2% by volume, frequently from 0.1 to 1% by volume;
transbutene-2≦1% by volume, preferably ≦0.5% by volume, frequently ≧0.003% by volume, ≦0.1% by volume;
cis-butene-2≦1% by volume, preferably ≦0.5% by volume, frequently ≧0.003% by volume, ≦0.1% by volume;
butene-1≦1% by volume, preferably ≦0.5% by volume, frequently ≧0.003% by volume, ≦0.1% by volume;
isobutene ≦1% by volume, preferably ≦0.5% by volume, frequently ≧0.003% by volume, ≦0.1% by volume;
butadiene-1,3≦1% by volume, preferably ≦0.5% by volume, frequently ≧0.003% by volume, ≦0.1% by volume;
butadiene-1,2≦1% by volume, preferably ≦0.5% by volume, frequently from ≧0 to 0.1% by volume;
butyne-1≦0.5% by volume, preferably ≦0.3% by volume, frequently from 0 to 0.1% by volume; and
butyne-2≦0.5% by volume, preferably ≦0.3% by volume, frequently from 0 to 0.1% by volume.

Gas mixtures 2 suitable according to the invention are also those which fulfill not only the abovementioned specifications, but also at the same time fulfill the following specifications:

other unsaturated $C_4$-hydrocarbons in total ≦0.5% by volume, preferably ≦0.3% by volume, frequently from 0 to 0.1% by volume;
$C_5$-hydrocarbons a total of ≦0.1% by volume, usually ≦0.05% by volume, generally from 0 to 300 ppm by volume;
$C_6$- to $C_8$-hydrocarbons in total ≦200 ppm by volume, usually <150 ppm by volume, generally from 0 to 30 ppm by volume;
acetone ≦100 ppm by volume;
$C_1$- to $C_4$-alcohols ≦100 ppm by volume;
$C_2$- to $C_4$-aldehydes ≦100 ppm by volume;
acetylene ≦10 ppm by volume;
carbonyl-containing compounds in total (calculated as $Ni(CO)_4$)≦100 ppm by volume;
ionic chlorine ≦1 mg/kg, generally from 0 to 0.2 mg/kg;
Cl-containing compounds in total and expressed as Cl ≦1 mg/kg, generally from 0 to 0.2 mg/kg;
F-containing compounds in total and expressed as F ≦1 mg/kg, generally from 0 to 0.2 mg/kg; and
S-containing compounds in total and expressed as S ≦10 mg/kg, frequently from 0 to 1 mg/kg, generally from 0 to 0.1 mg/kg;
with the proviso that in all the abovementioned cases, the total content of all $C_4$-hydrocarbons is ≦3% by volume (more preferably ≦2% by volume and most preferably ≦1% by volume) and the total content of butenes is at the same time more preferably ≦1% by volume (preferably ≦0.75% by volume and more preferably ≦0.5% by volume).

Nonspecified components (constituents) are preferably not present in the gas mixtures 2 according to the invention, i.e. not detectable.

For the purposes of the present invention, such gas mixtures 2, in particular when applying the separating processes mentioned for converting gas mixtures 1 to inventive gas mixtures 1', are generally also obtainable by using crude propanes in the first step which contain $\geq 100$ ppm by weight, or $\geq 150$ ppm by weight, or $\geq 200$ ppm by weight of $C_4$-hydrocarbons, or, for example, up to 6% by volume (for example from 0.1% by volume or 0.5% by volume to 6% by volume), especially when they fulfill the following specification:

propane content $\geq 90$% by volume, usually $\geq 93$% by volume, generally $\geq 95$% by volume;
propane and propylene content $\leq 99.75$% by volume or $\leq 99.5$% by volume, usually $\leq 99$% by volume or $\leq 98$% by volume, generally $\leq 97$% by volume;
total content of $C_4$-hydrocarbons $\leq 6$% by volume, usually $\leq 5$% by volume, generally $\leq 4$% by volume; but frequently $\geq 0.5$% by volume, or $\geq 1$% by volume, sometimes $\geq 2$% by volume, or in some cases $\geq 3$% by volume;
butene-1 content $\leq 0.5$% by volume, usually $\leq 0.3$% by volume, generally $\leq 0.1$% by volume; but frequently $\geq 5$ ppm by volume, sometimes $\geq 10$ ppm by volume, or in some cases $\geq 20$ ppm by volume;
total content of butenes $\leq 0.5$% by volume, usually $\leq 0.3$% by volume, generally $\leq 0.1$% by volume; but frequently $\geq 10$ ppm by volume, sometimes $\geq 20$ ppm by volume, or in some cases $\geq 30$ ppm by volume;
ethane content $\leq 10$% by volume, usually $\leq 5$% by volume, generally from 0 to 2% by volume;
ethylene content $\leq 5$% by volume, usually $\leq 2$% by volume, generally from 0 to 0.5% by volume;
methane content $\leq 5$% by volume, usually $\leq 2$% by volume, generally from 0 to 0.2% by volume;
cyclopropane content $\leq 0.1$% by volume;
propylene content $\leq 10$% by volume, usually $\leq 5$% by volume, generally $\leq 2$% by volume;
total content of $C_3$-hydrocarbons other than propane and propylene $\leq 0.3$% by volume;
total content of $C_5$-hydrocarbons $\leq 0.3$% by volume; and
total content of $C_6$- to $C_8$-hydrocarbons $\leq 600$ ppm by volume.

Crude propanes suitable according to the invention are also those which fulfill not only the abovementioned specifications, but also at the same time fulfill the following specifications:
total content of oxygen-containing compounds $\leq 300$ ppm by volume;
acetylene content $\leq 30$ ppm by volume;
ionic chlorine content $\leq 1$ mg/kg;
total content of Cl-containing compounds expressed as Cl <1 mg/kg;
total content of F-containing compounds expressed as F$\leq 1$ mg/kg;
total content of S-containing compounds expressed as S$\leq 10$ mg/kg (in the case of catalytic dehydrogenations, it may be advantageous when the reaction mixture, based on propane contained therein, contains from 1 to 1000 ppm by volume, preferably from 1 to 100 ppm by volume, of sulfur-containing compounds (e.g. $H_2S$ and/or dimethyl sulfide), since these, on the one hand, passivate steel components (of the reactor) such as Ni, Cr and Fe (which reduces undesired cracking of propane) and, on the other hand, are capable of activating the catalysts used (cf. "Catalytic dehydrogenation of lower alkanes, Resasco, Daniel E.; Haller, Gary L., University of Oklahoma, USA, Catalysis (1994), 11, 379-411");
with the proviso that the total content of $C_4$-hydrocarbons is preferably $\leq 3$% by volume, or $\leq 2.5$% by volume, or $\leq 2$% by volume, and the total content of butenes is more preferably at the same time 0.1% by volume.

The specifications of the crude propane defined under the proviso are generally suitable for the process according to the invention when the gas mixture 1, as a constituent of a gas mixture 2, is subjected as such to a heterogeneously catalyzed gas phase partial oxidation and/or a partial gas phase ammoxidation the propylene contained in gas mixture 1. In this connection, it is advantageous that a limited oxydehydrogenation and/or dehydrogenation conversion in the first step of the process according to the invention is favorable overall according to the invention. In general, this conversion, for each individual saturated hydrocarbon present, is at values of $\geq 5$ mol %, but <30 mol %, frequently $\leq 25$ mol % and in many cases $\leq 20$ mol %.

Normally, the above-specified, but also all other, crude propane suitable for the process according to the invention contains at least 0.25% by volume, or at least 0.5% by volume, or at least 1% by volume, frequently at least 1.5% by volume or at least 2% by volume and in many cases at least 2.5% by volume or at least 3% by volume, of constituents other than propane and propylene (but frequently $\leq 10$% by volume, usually $\leq 7$% by volume and generally $\leq 5$% by volume, of these constituents). These extraneous contents usually also apply to other crude propanes suitable for the process according to the invention, for example those which are free of $C_4$-hydrocarbons. However, these may also contain $\geq 0.1$% by volume, or $\geq 0.5$% by volume, frequently up to 6% by volume of $C_4$-hydrocarbons (e.g. from 0.1 or 0.5% by volume to 6% by volume). Also, and at the same time, they may contain $\geq 5$ ppm by volume, frequently up to 0.5% by volume of butenes (e.g. from 5 ppm by volume to 0.5% by volume). Further, they may at the same time also contain $\geq 5$ ppm by volume, frequently up to 0.5% by volume of butene-1 (e.g. from 5 ppm by volume to 0.5% by volume).

According to the invention, particularly suitable crude propanes are also those which fulfill not only the abovementioned specifications, but also at the same time the following specifications:
Ag $\leq 1$ μg/kg;
Al $\leq 10$ μg/kg;
As $\leq 1$ μg/kg;
Au $\leq 1$ μg/kg;
Ba $\leq 1$ μg/kg;
Be $\leq 1$ μg/kg;
Bi $\leq 1$ μg/kg;
Ca $\leq 2$ μg/kg;
Cd $\leq 1$ μg/kg;
Co $\leq 1$ μg/kg;
Cr $\leq 1$ μg/kg;
Cu $\leq 1$ μg/kg;
Fe $\leq 10$ μg/kg;
Ga $\leq 1$ μg/kg;
Ge $\leq 1$ μg/kg;
Hg $\leq 1$ μg/kg;
In $\leq 1$ μg/kg;
Ir $\leq 1$ μg/kg;
K $\leq 1$ μg/kg;
Li $\leq 1$ μg/kg;
Mg $\leq 1$ μg/kg;
Mn $\leq 1$ μg/kg;
Mo $\leq 1$ μg/kg;

Na ≦1 μg/kg;
Nb ≦1 μg/kg;
Ni ≦1 μg/kg;
Pb ≦1 μg/kg;
Pd ≦1 μg/kg;
Pt ≦1 μg/kg;
Rh ≦1 μg/kg;
Sb ≦1 μg/kg;
Sn ≦1 μg/kg;
Sr ≦1 μg/kg;
Ta ≦1 μg/kg;
Ti ≦1 μg/kg;
Tl ≦1 μg/kg;
V≦1 μg/kg;
Zn ≦1 μg/kg; and
Zr ≦1 μg/kg.

According to the invention, very particularly preferred crude propanes are those which not only fulfill the above-mentioned specifications, but also at the same time fulfill the following specifications:

density at 20° C.=500±2.0 kg/m³;
vapor pressure at 20° C.=7.6±0.2 bar;
water ≦10 mg/kg;
evaporation residue ≦2 mg/kg.

The specifications stated relate to determinations by means of gas chromatography and by means of atomic absorption spectroscopy. The vaporization residue relates to gravimetric determination. It generally consists of high-boiling hydrocarbons (e.g. green oil).

Unspecified constituents are preferably not present, i.e. not detectable, in the crude propanes preferably suitable according to the invention.

The procedure according to the invention is of particular significance when it is applied in a recycle method.

In this case, the desired target product is removed from the gas phase partial oxidation and/or ammoxidation product gas mixture by one of the known separating processes, and at least unconverted propane contained in this product gas mixture, generally together with unconverted propylene contained therein, is recycled into the oxydehydrogenation and/or dehydrogenation step and/or into the gas phase partial oxidation and/or ammoxidation. Customarily, this recycling (circulation) of the propane and propylene as a constituent of the residual gas remaining after the target product removal is effected without intermediately treating the residual gas, or, when it is intermediately treated (for example removal of CO, $CO_2$, $H_2$ and/or $O_2$ contained therein before recycling), this intermediate treatment is practiced only with limited cost and inconvenience. In other words, even when the crude propane used only contains small proportions of $C_4$-hydrocarbons, for example n-butane, iso-butane, butene-1 or other butenes (for example total content of $C_4$-hydrocarbons ≧0.01% by volume, possibly up to 6% by volume), these may accumulate in gas mixture 2 in a recycle gas method and exceed the limits according to the invention unless special measures are taken. These methods may involve, for example, specifically removing the $C_4$-hydrocarbons from the residual gas remaining after the target product removal rectificatively and/or by absorption/desorption and/or stripping and/or by adsorption/desorption and/or by condensation and/or by membrane processes, and only then recirculating the propane- and propylene-containing residual gas remaining thereafter.

EP-A 938463 regards such a separating step as unnecessary, even though it recommends using gas mixture 1 as such for the partial oxidation and using crude propane of substantially any desired purity for the first step.

Alternatively to a recycle method, the residual gases may also be fed to other uses to avoid undesired accumulations of $C_4$-hydrocarbons. For example, they may be combusted together with the propane and propylene contained therein for the purposes of electricity generation and/or be used for preparing synthesis gas, among other uses.

Otherwise, the process according to the invention may be carried out in a similar manner to the different basic variants described in the prior art.

In other words, in the simplest variant, all steps of the process according to the invention are carried out in a single reaction zone and over a catalyst charge present in it, as taught, for example, in the documents EP-A 608838, EP-A 529853, DE-A 19835247, EP-A 895809, JP-A 7-232071, JP-A 11-169716, EP-A 1192987, JP-A 10-57813, JP-A 2000-37623, JP-A 10-36311, WO 00/29105, EP-A 767164, DE-A 10029338, JP-A 8-57319, JP-A 10-28862, JP-A 11-43314, JP-A 11-574719, WO 00/29106, JP-A 10-330343, JP-A 11-285637, JP-A 310539, JP-A 11-42434, JP-A 11-343261, JP-A 3423262, WO 99/03825, JP-A 7-53448, JP-A 2000-51693, JP-A 11-263745, DE-A 10046672, DE-A 10118814, DE-A 10119933, JP-A 2000/143,244, EP-A 318295, EP-A 603836, DE-A 19832033, DE-A 19836359, EP-A 962253, DE-A 10119933, DE-A 10051419, DE-A 10046672, DE-A 10033121, DE-A 101 459 58, DE-A 10122027, EP-A 1193240 and the literature cited in these documents.

The active composition of the catalyst charge to be used is substantially a multimetal oxide composition which comprises the elements Mo and V, at least one of the two elements Te and Sb and at least one of the elements from the group comprising Nb, Ta, W, Ti, Al, Zr, Cr, Mn, Ga, Fe, Ru, Co, Rh, Ni, Pd, Pt, La, Bi, B, Ce, Sn, Zn, Si, Na, Li, K, Mg, Ag, Au and In in combination.

Preferably, the combination of the latter element group comprises the elements Nb, Ta, W and/or Ti, and more preferably the element Nb.

Preferably, the relevant multimetal oxide active compositions comprise the abovementioned element combination in the stoichiometry I

$$Mo_1V_bM^1_cM^2_d \quad\quad (I),$$

where
$M^1$=Te and/or Sb,
$M^2$=at least one of the elements from the group comprising Nb, Ta, W, Ti, Al, Zr, Cr, Mn, Ga, Fe, Ru, Co, Rh, Ni, Pd, Pt, La, Bi, Ce, Sn, Zn, Si, Na, Li, K, Mg, Ag, Au and In,
b=from 0.01 to 1,
c=from ≧0 to 1, and
d=from ≧0 to 1.

Preferably, according to the invention, $M^1$=Te and $M^2$=Nb, Ta, W and/or Ti. Preferably, $M^2$=Nb.

The stoichiometric coefficient b is advantageously from 0.1 to 0.6. Correspondingly, the preferred range for the stoichiometric coefficient c extends from 0.01 to 1 or from 0.05 to 0.4 and advantageous values for d are from 0.01 to 1 or from 0.1 to 0.6.

According to the invention, it is particularly advantageous when the stoichiometric coefficients b, c and d simultaneously lie within the abovementioned preferred ranges.

That which was said above applies in particular when the active composition of the catalyst charge consists of one of the abovementioned element combinations with regard to its elements other than oxygen.

These are then in particular the multimetal oxide active compositions of the general stoichiometry II $$Mo_1V_bM^1_cM^2_dO_n \quad (II)$$

where the variables are each as defined with regard to the stoichiometry I and n=a number which is determined by the valency and frequency of the elements other than oxygen in (II).

In the one-zone method for the process according to the invention, preference is further given to using those multimetal oxide active compositions which, on the one hand, either contain one of the abovementioned element combinations or, with regard to the elements other than oxygen, consist of them and, at the same time, have an X-ray diffractogram which exhibits reflections h and i whose peak locations are at the reflection angles (2θ) of 22.2±0.5° (h) and 27.3±0.50° (i) (all the information relating to an X-ray diffractogram in this document relates to an X-ray diffractogram obtained using Cu—Kα radiation as the X-ray radiation (theta-theta D-5000 Siemens diffractometer, tube voltage: 40 kV, tube current: 40 mA, aperture V20 (variable), collimator V20 (variable), secondary monochromator aperture (0.1 mm), detector aperture (0.6 mm), measuring intervale (2θ): 0.02°, measurement time per step: 2.4 s, detector: scintillation counting tube).

The half-height width of these reflections may be very small or else very marked.

For the process according to the invention, particular preference is given to those of the abovementioned multimetal oxide active compositions whose X-ray diffractogram, in addition to the reflections h and i, has a reflection k whose peak location is at 28.2±0.5° (k).

Among the latter, preference is given according to the invention in turn to those in which the reflection h has the highest intensity within the X-ray diffractogram, and also a maximum half-height width of 0.5°, and very particular preference is given to those in which the half-height width of the reflection i and of the reflection k are at the same time ≦1° and the intensity $P_k$ of the reflection k and the intensity $P_i$ of the reflection i fulfill the relationship 0.2≦R≦0.85, better 0.3≦R≦0.85, preferably 0.4≦R≦0.85, particularly preferably 0.65≦R<0.85, even more preferably 0.67≦R≦0.75 and very particularly preferably R=from 0.70 to 0.75 or R=0.72 where R is the intensity ratio defined by the formula $$R=P_i/(P_i+P_k)$$

Preferably, the abovementioned X-ray diffractograms have no reflection whose maximum is at 2θ=50±0.3°.

The definition of the intensity of a reflection in the X-ray diffractogram in this document refers to the definition laid down in DE-A 19835247, DE-A 10122027, and also in DE-A 10051419 and DE-A 10046672. The same applies to the definition of the half-height width.

In addition to the reflections h, i and k, the abovementioned X-ray diffractograms of multimetal oxide active compositions to be used advantageously according to the invention contain still further reflections whose peak locations are at the following reflection angles (2θ):
9.0±0.4° (l)
6.7±0.4° (o) and
7.9±0.4° (p).

It is further advantageous when the X-ray diffractogram additionally contains a reflection angle whose peak location is at a reflection angle (2θ)=45.2±0.4° (q).

Frequently, the X-ray diffractogram also contains the reflections 29.2±0.40 (m) and 35.4±0.4° (n).

It is further advantageous when the element combinations defined in the formulae I and II are present as a pure i-phase. When the catalytically active oxide composition also contains k-phase, its X-ray diffractogram contains, in addition to the above-mentioned reflections, further reflections whose peak locations are at the following reflection angles (2θ): 36.2±0.4° and 50±0.4° (the terms i- and k-phase are used in this document as defined in DE-A 10122027 and DE-A 10119933).

When the intensity 100 is assigned to the reflection h, it is advantageous according to the invention when the reflections i, l, m, n, o, p and q on the same intensity scale have the following intensities:
i: from 5 to 95, frequently from 5 to 80, sometimes from 10 to 60;
l: from 1 to 30;
m: from 1 to 40;
n: from 1 to 40;
o: from 1 to 30;
p: from 1 to 30 and
q: from 5 to 60.

When the X-ray diffractogram contains of the above-mentioned additional reflections, their half-height width is generally ≦1°.

The specific surface area of multimetal oxide active compositions of the general formula II to be used according to the invention or of multimetal oxide active compositions which contain element combinations of the general formula I is in many cases from 1 to 30 m²/g (BET surface area, nitrogen), in particular when their X-ray diffractogram is as described.

The preparation of the multimetal oxide active compositions described can be found in connection with this cited prior art. This includes in particular DE-A 10122027, DE-A 10119933, DE-A 10033121, EP-A 1192987, DE-A 10029338, JP-A 2000-143244, EP-A 962253, EP-A 895809, DE-A 19835247, WO 00/29105, WO 00/29106, EP-A 529853 and EP-A 608838 (in all implementation examples of the last two documents, the drying method to be applied is spray drying; for example, at an entrance temperature of from 300 to 350° C. and an exit temperature of from 100 to 150° C.; cocurrent or countercurrent).

The multimetal oxide active compositions described may be used as such (i.e. in powder form) or shaped to suitable geometries (cf., for example, the coated catalysts of DE-A 10051419 and also the geometric variants of DE-A 10122027) for the one-zone configuration of the process according to the invention. They are suitable in particular for preparing acrolein and/or acrylic acid and also for preparing acrylonitrile.

The basis of the one-zone method is that the catalysts to be used are capable of catalyzing all steps of the process according to the invention.

They may be carried out either in a fixed catalyst bed or in a fluidized catalyst bed (moving bed). Appropriate process descriptions can be found in the prior art documents. When the process according to the invention is implemented as a fixed-bed reaction, for example for preparing acrylic acid in the one-zone method, it is advantageously carried-out in a tube bundle reactor whose catalyst tubes are charged with the catalyst. Normally, a liquid, generally a salt melt, is conducted as a heat carrier around the catalyst tubes. Alternatively, a thermoplate reactor may be used, in which case the catalyst charge is disposed as a flat arrangement between cooling plates.

The reaction gas mixture, viewed in the catalyst tubes over the reactor, is conducted either in cocurrent or in countercurrent to the salt bath. The salt bath itself may practice a pure parallel flow relative to the catalyst tubes. However, it will be appreciated that a crossflow may also be superimposed thereupon. Overall, the salt bath may practice a meandering flow around the catalyst tubes which is only conducted in cocurrent or in countercurrent to the reaction gas mixture when viewed over the reactor. Tube bundle reactors suitable for the process according to the invention are disclosed, for example, by the documents EP-A 700714 and EP-A 700893.

The different possible compositions of the reaction gas mixture for the one-zone variant of the process according to the invention may be taken from the prior art cited in connection with this process variant.

For the preparation of acrylic acid, the composition of the starting reaction gas mixture typically varies within the following range (molar ratios):

propane:oxygen:$H_2O$:other constituents (in particular inert diluent gases)=1:(0.1-10):(>0-50):(>0-50).

Preferably, the abovementioned ratio is 1:(0.5-5):(1-30):(1-30).

The abovementioned ranges apply in particular when the other constituents used are predominantly molecular nitrogen. The reaction temperature is typically from 250 to 550° C. (the conditions for the ammoxidation are comparable, apart from the fact that the reaction gas mixture additionally comprises ammonia (cf., for example, EP-A 929853)).

The loading of a fixed bed catalyst charge with propane in the case of the one-zone variant of the process according to the invention may be, for example, from 10 to 500 l (STP)/l (fixed bed)·h. The loading with starting reaction gas mixture is frequently in the range from 100 to 10000 l (STP)/l·h, in many cases in the range from 500 to 5000 l (STP)/l·h.

The target product, for example acrylic acid, may be removed from the resulting product gas mixture in a manner known per se, as described, for example, in DE-A 10122027. In other words, the acrylic acid present may be taken up from the product gas mixture, for example, by absorption with a high-boiling inert hydrophobic organic solvent (e.g. a mixture of diphenyl ether and diphenyl which may optionally also contain additives such as dimethyl phthalate). The resulting mixture of absorbent and acrylic acid may subsequently be rectificatively, extractively and/or crystallizatively worked up in a manner known per se to give glacial acrylic acid. Alternatively, the basic removal of the acrylic acid from the product gas mixture may also be effected by fractional condensation, as described, for example, in DE-A 10053086, DE-A 19627847, DE-A 19740253, DE-A 19740252, DE-A 19606877 and DE-A 19740253. The resulting acrylic acid condensate may be further purified, for example, by fractional crystallization (e.g. suspension crystallization and/or layer crystallization).

The residual gas mixture remaining after the basic removal of the acrylic acid contains in particular unconverted propane, with or without unconverted propylene.

Depending on the butene-1 content of this residual gas mixture and its total content of butenes and $C_4$-hydrocarbons, and on the oxygen source used (whether pure oxygen, an oxygen-containing inert gas or air), the reaction mixture may be recycled as such. If desired, it will also be divided into two portions of identical composition, and only one portion will be recycled and the other portion purged (for example fed to its combustion or another use (e.g. synthesis gas preparation)). It will be appreciated that the latter could also be effected using the entirety of residual gas mixture.

In the case of increased portions of the $C_4$ components undesirable according to the invention and/or increased proportions of other undesired components in the residual gas mixture, the propane and any propene contained in the residual gas mixture may be removed, for example by fractional pressure rectification (the separating factor may be selected appropriately), and then recycled into the process according to the invention and combined with the crude propane and other constituents of the starting reaction gas mixture. However, from the inventive standpoint, it may suffice if desired to contact the residual gas in an extraction device with a preferably $C_3$-hydrocarbon-absorbing hydrophobic organic solvent (e.g. by passing it through). By subsequent desorption and/or stripping with air (which will be required as an oxygen source in any case), the absorbed propane and any propene may be released again and recycled into the process according to the invention. It will be appreciated that the acrylic acid could also be removed from the product mixture by the procedure described in DE-A 10059122. It will be appreciated that the multimetal active compositions recommended for the one-zone method may also be used in the process according to the invention in diluted form with finely divided, e.g. colloidal, materials such as silicon dioxide, titanium dioxide, aluminum oxide, zirconium oxide and niobium oxide.

The dilution mass ratio may be up to 9 (diluent):1 (active composition). In other words, examples of possible diluent mass ratios include 6 (diluent):1 (active composition) and 3 (diluent):1 (active composition). The diluent may be incorporated in accordance with DE-A 10122027 before or after calcination. However, it will be appreciated that it is also possible to use other catalyst systems for the one-zone method according to the invention, as described, for example, by JP-A 3-170445.

When the process according to the invention is realized in one reaction zone, one of the cases is that in which gas mixture 1 and gas mixture 2 are identical. The process according to the invention is used in particular when the content limits according to the invention for $C_4$-hydrocarbons in the product gas mixture of the process according to the invention are exceeded.

According to the invention, preference is given to realizing the process according to the invention in more than one reaction zone, as described, for example, in EP-A 938463, EP-A 117146, DE-A 3313573, GB-A 2118939, U.S. Pat. No. 3,161,670, WO 01/96270, EP-A 731077, DE-A 19837520, DE-A 19837517, DE-A 19837519, DE-A 19837518, DE-A 19837520, DE-A 10131297 and DE-A 10211275.

More than one reaction zone means primarily that at least one step of the process according to the invention is carried out under conditions which may be selected at least partially independently of those of the at least one other step within the process according to the invention, or, although only secondarily, that at least partially independent reaction conditions may be realized within one and the same step along the reaction path (the latter is the case, for example, when multizone methods are used for one step (having temperature zones which can be adjusted independently), as described, for example, in DE-A 19948241, DE-A 19927624, DE-A 19910508, DE-A 19910506 and DE-A 19948248). In other words, when the process according to the invention comprises, for example, two steps, the first step could be carried out, for example, using another catalyst or another catalyst charge than for the second step. Or, another procedure could be to use identical catalysts or catalyst charges for both steps but to select and adjust the reaction temperatures for the two steps independently of one another. It will be appreciated that both measures may also be superimposed.

The advantage of the multizone method is based on the fact that it in principle allows an improved adaptation of the reaction conditions to the requirements of the individual steps of the process according to the invention.

This advantage is well-known from the heterogeneously catalyzed gas phase partial oxidation of propylene to acrylic acid using molecular oxygen.

In principle, it proceeds along the reaction coordinate in two successive steps along the reaction coordinate, of which the first leads to acrolein and the second from acrolein to acrylic acid.

This reaction sequence in a manner known per se opens up the possibility of implementing the partial oxidation according to the invention of the propylene contained in gas mixture 2 in two oxidation zones arranged in succession, and allows the oxidic catalyst to be used in each of the two oxidation zones to be optimized (this optimization opportunity also allows the partial oxidation of the propylene to be stopped at the acrolein and the acrolein to be isolated). For instance, the preferred catalyst for the first oxidation zone (propylene→acrolein) is generally a multimetal oxide based on the element combination Mo—Bi—Fe, while the catalyst preferred for the second oxidation zone (acrolein→acrylic acid) is normally a multimetal oxide based on the element combination Mo—V (for example also those which have been recommended in this document for the one-zone method). However, these two reaction steps may in principle also be carried out in a single reaction zone and over a single catalyst.

Quite generally, the first step in the process according to the invention will advantageously be carried out in a separate reaction zone.

In the case of an oxydehydrogenation of propane, this may be carried out in the gas phase as a homogeneously and/or heterogeneously catalyzed oxydehydrogenation of propane to propylene using molecular oxygen. The source of the molecular oxygen used may be air, pure molecular oxygen or air enriched with molecular oxygen.

When the reaction zone is configured as a homogeneous oxydehydrogenation, this can in principle be carried out in such a way as described, for example, in the documents U.S. Pat. No. 3,798,283, CN-A 1 105 352, Applied Catalysis, 70(2)1991, pp. 175-187, Catalysis Today 13, 1992, pp. 673-678 and in the application DE-A 19 622 331. An advantageous oxygen source is air. The temperature of the homogeneous oxydehydrogenation is advantageously selected within the range from 300 to 700° C., preferably within the range from 400 to 600° C., more preferably in the range from 400 to 500° C. The working pressure may be from 0.5 to 100 bar, in particular from 1 to 10 bar. The residence time is typically from 0.1 or 0.5 to 20 seconds, preferably from 0.1 or 0.5 to 5 seconds.

The reactor used may be, for example, a tube furnace or a tube bundle reactor, for example a countercurrent tube furnace using flue gas as the heat carrier or a tube bundle reactor using a salt melt as the heat carrier. The propane to oxygen ratio in the starting mixture is preferably from 0.5:1 to 40:1, in particular between 1:1 and 6:1, more preferably between 2:1 and 5:1. The starting mixture may also comprise further, preferably inert (in this document, inert constituents preferably refer quite generally to those constituents of which less than 5 mol %, preferably less than 3 mol % and more preferably less than 1 mol % react in the relevant reaction step; most preferably, they do not react at all), constituents such as water, carbon dioxide, carbon monoxide, nitrogen, noble gases, other hydrocarbons (e.g. secondary components present in the crude propane), and/or propylene, etc., also including recycled (cycle gas) constituents.

When the propane dehydrogenation is configured as a heterogeneously catalyzed oxydehydrogenation, this can in principle be carried out as described, for example, in the documents U.S. Pat. No. 4,788,371, CN-A 1073893, Catalysis Letters 23 (1994), 103-106, W. Zhang, Gaodeng Xuexiao Huaxue Xuebao, 14 (1993) 566, Z. Huang, Shiyou Huagong, 21 (1992) 592, WO 97/36849, DE-A 197 53 817, U.S. Pat. No. 3,862,256, U.S. Pat. No. 3,887,631, DE-A 195 30 454, U.S. Pat. No. 4,341,664, J. of Catalysis 167, 560-569 (1997), J. of Catalysis 167, 550-559 (1997), Topics in Catalysis 3 (1996) 265-275, U.S. Pat. No. 5,086,032, Catalysis Letters 10 (1991), 181-192, Ind. Eng. Chem. Res. 1996, 35, 14-18, U.S. Pat. No. 4,255,284, Applied Catalysis A: General, 100 (1993), 111-130, J. of Catalysis 148, 56-67 (1994), V. Cortés Corberán and S. Vic Bellón (Ed.), New Developments in Selective Oxidation II, 1994, Elsevier Science B. V., S. 305-313, 3$^{rd}$ World Congress on Oxidation Catalysis, R. K. Grasselli, S. T. Oyama, A. M. Gaffney and J. E. Lyons (Ed.), 1997, Elsevier Science B. V., p. 375 ff. or in DE-A 19837520, DE-A 19837517, DE-A 19837519 and DE-A 19837518. The oxygen source used may also be air. However, the oxygen source consists frequently of at least 90 mol % of molecular oxygen, and in many cases at least 95 mol % of oxygen.

The catalysts suitable for the heterogeneously catalyzed oxydehydrogenation are subject to no particular restrictions. Useful catalysts are any oxydehydrogenation catalysts known to those skilled in the art which are capable of oxidizing propane to propylene. In particular, any oxydehydrogenation catalysts specified in the documents cited above may be used. Examples of suitable catalysts include oxydehydrogenation catalysts which comprise the MoVNb oxides or vanadyl pyrophosphate, optionally with promoter. An example of such an advantageous oxydehydrogenation catalyst is a catalyst as also recommended for the one-zone method which comprises a mixed metal oxide comprising Mo, V, Te, O and X as essential constituents where X is at least one element selected from niobium, tantalum, tungsten, titanium, aluminum, zirconium, chromium, manganese, gallium, iron, ruthenium, cobalt, rhodium, nickel, palladium, platinum, antimony, bismuth, boron, indium, silicon, lanthanum, sodium, lithium, potassium, magnesium, silver, gold and cerium (on this subject, see also EP-A 938463 and EP-A 167109). Further particularly suitable oxydehydrogenation catalysts are the multimetal oxide compositions or catalysts A of DE-A-197 53 817 and the catalysts of DE-A 19838312, and the multimetal oxide compositions or catalysts A in the former document mentioned as being preferable are very particularly advantageous. In other words, useful active compositions are in particular multimetal oxide compositions of the general formula III

$$M^1{}_a MO_{1-b} M^2{}_b O_x \qquad (III)$$

where $M^1$=Co, Ni, Mg, Zn, Mn and/or Cu, $M^2$=W, V, Te, Nb, P, Cr, Fe, Sb, Ce, Sn and/or La, a=0.5-1.5 b=0-0.5 and x=a number which is determined by the valency and frequency of the elements other than oxygen in (III).

In principle, suitable active compositions (III) can be prepared in a simple manner by generating from suitable sources of their elemental constituents a very intimate, preferably finely divided dry mixture corresponding to its stoichiometry and calcining it at temperatures of from 450 to 1000° C. Useful sources for the elemental constituents of the multimetal oxide active compositions (III) are those compounds which are already oxides and/or those compounds which can be converted to oxides by heating, at least in the presence of oxygen. These are in particular halides, nitrates, formates, oxalates, citrates, acetates, carbonates, ammine complex salts, ammonium salts and/or hydroxides. The starting compounds for preparing the multimetal oxide compositions (III) may be intimately mixed in dry form, for example as a finely divided powder, or in wet form, for example with water as a solvent. The multimetal oxide compositions (III) may be used either in powder form or else shaped to certain catalyst geometries, and the shaping may be effected before or after the final calcining. It is also possible to use unsupported catalysts. However, a pulverulent active composition or precursor composition may also be shaped by applying to preshaped inert catalyst supports. Useful catalyst supports are customary, porous or nonporous aluminum oxides, silicon dioxide, thorium dioxide, zirconium dioxide, silicon carbide or silicates, and the support bodies may be regularly or irregularly shaped.

For the heterogeneously catalyzed oxydehydrogenation of propane, the reaction temperature is preferably in the range from 200 to 600° C., in particular in the range from 250 to 500° C., more preferably in the range from 350 to 440° C. The working pressure is preferably in the range from 0.5 to 10 bar, in particular from 1 to 10 bar, more preferably from 1 to 5 bar working pressures of above 1 bar, for example from 1.5 to 10 bar, have proven particularly advantageous. In general, heterogeneously catalyzed oxydehydrogenation of propane is effected over a fixed catalyst bed. The latter is advantageously charged into the tubes of a tube bundle reactor, as described, for example, in EP-A-0 700 893 and EP-A-0 700 714 and also in the literature cited in these documents. The average residence time of the reaction gas mixture in the catalyst bed is advantageously from 0.5 to 20 seconds. The ratio of propane to oxygen varies with the desired conversion and selectivity of the catalyst, and is advantageously in the range from 0.5:1 to 40:1, in particular from 1:1 to 6:1, more preferably from 2:1 to 5:1. In general, the propylene selectivity falls with rising propane conversion. The propane to propylene reaction is therefore preferably carried out in such a way that relatively low conversions of propane are achieved at high selectivities for propylene. The conversion of propane is more preferably in the range from 5 to 40 mol %, frequently in the range from 10 to 30 mol %. In this connection, the term "propane conversion" means the proportion of propane fed (sum of propane contained in the crude propane and any recycled recycle gas which is converted in a single pass). In general, the selectivity of the propylene formation is from 50 to 98 mol %, more preferably from 80 to 98 mol %, where the term "selectivity" refers to the moles of propylene generated per mole of reacted propane, expressed as a molar percentage.

In general, the starting mixture used in the oxidative propane dehydrogenation comprises from 5 to 95 mol % of propane (based on 100 mol % of starting mixture). In addition to propane and oxygen, the starting mixture for the heterogeneously catalyzed oxydehydrogenation may also comprise further, in particular inert, constituents such as carbon dioxide, carbon monoxide, nitrogen, noble gases, other hydrocarbons, e.g. secondary components present in the crude propane, and/or propylene. The heterogeneous oxydehydrogenation may also be carried out in the presence of diluents, for example steam.

Any desired reactor sequence known to those skilled in the art may be used for carrying out the homogeneous oxydehydrogenation or the heterogeneously catalyzed oxydehydrogenation of propane. For example, the oxydehydrogenation may be carried out in a single reactor or in a battery of two or more reactors, between which oxygen is optionally introduced. The possibility also exists of practicing the homogeneous and the heterogeneously catalyzed oxydehydrogenation combined with each other.

Examples of possible constituents contained in the product mixture of a propane oxydehydrogenation according to the invention include the following components: propylene, propane, carbon dioxide, carbon monoxide, water, nitrogen, oxygen, ethane, ethene, methane, acrolein, acrylic acid, ethylene oxide, butane (e.g. n-butane or isobutane), acetic acid, formaldehyde, formic acid, propylene oxide and butenes (e.g. butene-1). Typically, a product mixture obtained in the propane oxydehydrogenation according to the invention comprises: from 5 to 10 mol % of propylene, from 0.1 to 2 mol % of carbon monoxide, from 1 to 3 mol % of carbon dioxide, from 4 to 10 mol % of water, from 0 to 1 mol % of nitrogen, from 0.1 to 0.5 mol % of acrolein, from 0 to 1 mol % of acrylic acid, from 0.05 to 0.2 mol % of acetic acid, from 0.01 to 0.05 mol % of formaldehyde, from 1 to 5 mol % of oxygen, from 0.1 to 1.0 mol % of further above-mentioned components, and also a remainder of substantially propane, based in each case on 100 mol % of product mixture.

In general, the propane dehydrogenation in the first reaction zone may also be carried out as a heterogeneously catalyzed propane dehydrogenation with substantial exclusion of oxygen as described in DE-A 3313573, WO 01/96270, DE-A 10131297 or DE-A 10211275, or as follows:

Since the heterogeneously catalyzed dehydrogenation reaction proceeds with increasing volume, the conversion may be increased by reducing the partial pressure of the products. This can be achieved in a simple manner, for example by dehydrogenating at reduced pressure and/or by admixing substantially inert diluent gases, for example steam, which normally constitutes an inert gas for the dehydrogenation reaction. Dilution with steam generally results in the further advantage of reduced carbonization of the catalyst used, since the steam reacts by the principle of coal gasification with carbon formed. Also, steam may be used as a diluent gas in the subsequent at least one oxidation and/or ammoxidation zone (also referred to in this document for short as at least one partial zone). However, steam may also be partially or completely removed from the dehydrogenation product mixture in a simple manner (for example by condensing), which opens up the possibility of increasing the proportion of the diluent gas $N_2$ in the further use of the modified product mixture obtained in this way in the at least one partial zone. Examples of further suitable diluents for the heterogeneously catalyzed propane dehydrogenation include CO, methane, ethane, $CO_2$, nitrogen and noble gases such as He, Ne and Ar. All diluents specified may be used either alone or in the form of highly differing mixtures. It is advantageous that the diluents specified are generally also suitable diluents in the at least one partial zone. Generally, as already stated, preference is given to diluents which behave inertly in the particular reaction zone (i.e. of which less than 5 mol %, preferably less than 3 mol % and even better less than 1 mol %, chemically change). In principle, useful catalysts for the heterogeneously catalyzed propane dehydrogenation are all dehydrogenation catalysts known from the prior art. They can be roughly divided into two groups, i.e. into those which are of an oxidic nature (for example chromium oxide and/or aluminum oxide) and into those which consist of at least one generally comparatively noble metal (for example platinum) deposited on a generally oxidic support.

Some of the dehydrogenation catalysts which can be used are all those recommended in WO 01/96270, EP-A 731077, DE-A 10211275, DE-A 10131297, wO 99/46039, U.S. Pat. No. 4,788,371, EP-A-0 705 136, WO 99/29420, U.S. Pat. No. 4,220,091, U.S. Pat. No. 5,430,220, U.S. Pat. No. 5,877,369, EP-A-0 117 146, DE-A 199 37 196, DE-A 199 37 105 and DE-A 199 37 107. In particular, the catalyst of Example 1, Example 2, Example 3 and Example 4 of DE-A 199 37 107 may be used.

These are dehydrogenation catalysts which comprise from 10 to 99.9% by weight of zirconium dioxide, from 0 to 60% by weight of aluminum oxide, silicon dioxide and/or titanium dioxide and from 0.1 to 10% by weight of at least one element of the first or second main group, of an element of the third transition group, of an element of the eighth transition group of the Periodic Table, lanthanum and/or tin, with the proviso that the sum of the percentages by weight is 100% by weight.

To carry out the heterogeneously catalyzed propane dehydrogenation, useful reactor types and process variants are all of those known from the prior art. Descriptions of such process variants are contained, for example, in all prior art documents cited in relation to the dehydrogenation catalysts.

A comparatively comprehensive description of dehydrogenation processes suitable according to the invention is also contained in "Catalytica ® Studies Division, Oxidative Dehydrogenation and Alternative Dehydrogenation Processes", Study Number 4192 OD, 1993, 430 Ferguson Drive, Mountain View, Calif., 94043-5272 U.S.A.

It is characteristic of the partial heterogeneously catalyzed dehydrogenation of propane that it proceeds endothermically. This means that the heat (energy) required for the attainment of the necessary reaction temperature has to be fed to the starting reaction gas mixture either beforehand and/or in the course of the heterogeneously catalyzed dehydrogenation.

Owing to the high reaction temperatures required, it is further typical, especially for heterogeneously catalyzed dehydrogenations of propane, that small amounts of high-boiling high molecular weight organic compounds, up to and including carbon, are formed which deposit on the catalyst surface and thus deactivate it. In order to minimize this disadvantageous accompanying phenomenon, the propane-containing reaction gas mixture to be passed over the catalyst surface at an elevated temperature for heterogeneously catalyzed dehydrogenation may be diluted with steam. Depositing carbon is partially or completely eliminated under the resulting conditions by the principle of coal gasification.

Another possibility of removing deposited carbon compounds involves allowing an oxygen-containing gas to flow through the dehydrogenation catalyst at elevated temperature from time to time and thus to effectively burn off the deposited carbon. However, a substantial suppression of formation of carbon deposits is also possible by adding molecular hydrogen to the propane to be dehydrogenated with heterogeneous catalysis before it is conducted over the dehydrogenation catalyst at elevated temperature.

It will be appreciated that the possibility also exists of adding steam and molecular hydrogen in a mixture to the propane to be dehydrogenated with heterogeneous catalysis. Addition of molecular hydrogen to the heterogeneously catalyzed dehydrogenation of propane also reduces the undesired by-production of allene (propadiene), propyne and acetylene.

A suitable form of reactor for the heterogeneously catalyzed propane dehydrogenation is a fixed bed tubular or tube bundle reactor. This means that the dehydrogenation catalyst is disposed as a fixed bed in one reaction tube or in a bundle of reaction tubes. The reaction tubes are heated by the combustion of a gas, for example a hydrocarbon such as methane, in the space surrounding the reaction tubes. It is advantageous to apply this direct form of catalyst tube heating only to about the first 20 to 30% of the fixed bed and to heat the remaining bed length to the required reaction temperature by the radiant heat released in the course of the combustion. In this way, virtually isothermal reaction control is achievable. Suitable internal diameters of reaction tubes are from about 10 to 15 cm. A typical dehydrogenation tube bundle reactor comprises from 300 to 1000 reaction tubes. The internal temperature in the reaction tubes varies within the range from 300 to 700° C., preferably within the range from 400 to 700° C. Advantageously, the starting reaction gas mixture is fed to the tubular reactor preheated to the reaction temperature. It is possible that the product gas mixture leaves the reaction tube at a temperature which is lower by from 50 to 100° C. However, this starting temperature may also be at a higher or at the same level. For the purposes of the above-mentioned procedure, it is advantageous to use oxidic dehydrogenation catalysts based on chromium oxide and/or aluminum oxide. Frequently, no diluent gas will be used, and the starting reaction gas will instead substantially be crude propane alone. The dehydrogenation catalyst is also usually used undiluted.

On the industrial scale, it is possible to operate a plurality of such tube bundle reactors (e.g. three) in parallel. According to the invention, two of these reactors may be in the dehydrogenation operation, while the catalyst charge is regenerated in a third reactor, without the operation in the at least one partial zone being effected.

Such a procedure is advantageous, for example, in the BASF-Linde propane dehydrogenation process known from the literature.

However, it is significant according to the invention that the use of such a tube bundle reactor is sufficient. Such a procedure can also be used in the "steam active reforming (STAR) process" which has been developed by Phillips Petroleum Co. (see, for example, U.S. Pat. No. 4,902,849, U.S. Pat. No. 4,996,387 and U.S. Pat. No. 5,389,342). The dehydrogenation catalyst used in the STAR process is advantageously platinum containing promoters on zinc (magnesium) spinel as the support (see, for example, U.S. Pat. No. 5,073,662). In contrast to the BASF-Linde propane dehydrogenation process, the propane to be dehydrogenated is diluted with steam in the STAR process. A typical molar ratio of steam to propane is in the range from 4 to 6. The starting reactor pressure is frequently from 3 to 8 atm and the reaction temperature is advantageously selected from 480 to 620° C. Typical liquid gas hourly space velocities (LHSV) with the total reaction gas mixture are at from 0.5 to 10 $h^{-1}$.

The heterogeneously catalyzed propane dehydrogenation may also be effected in a moving bed. For example, the moving catalyst bed may be accommodated in a radial flow reactor. In the reactor, the catalyst moves slowly from top to bottom while the reaction gas mixture flows radially. This procedure is applied, for example, in the UOP-Oleflex dehydrogenation process. Since the reactors in this process are operated virtually adiabatically, it is advantageous to operate a plurality of reactors connected in series as a battery (typically up to four). This allows excessively large differences in the temperatures of the reaction gas mixture at the reactor entrance and the reactor exit to be avoided (in the adiabatic mode of operation, the starting reaction gas mixture functions as a heat carrier, upon whose heat content the drop in the reaction temperature is dependent) but nevertheless allows attractive overall conversions to be achieved.

When the catalyst bed has left the moving bed reactor, it is fed to the regeneration and subsequently reused. The dehydrogenation catalyst used for this process may be, for example, a spherical dehydrogenation catalyst which consists substantially of platinum on spherical aluminum oxide support. In the UOP variant, hydrogen is added to the propane to be dehydrogenated, in order to avoid premature catalyst aging. The working pressure is typically from 2 to 5 atm. The (molar) hydrogen to propane ratio is advantageously from 0.1 to 1. The reaction temperatures are preferably from 550 to 650° C. and the contact time of catalyst with reaction gas mixture is selected from about 2 to 6 h$^{-1}$.

In the fixed bed processes described, the catalyst geometry may likewise be spherical, but also cylindrical (hollow or solid) or have a different geometry.

A further process variant for the heterogeneously catalyzed propane dehydrogenation described by Proceedings De Witt, Petrochem. Review, Houston, Tex., 1992 a, N1 is the possibility of a heterogeneously catalyzed propane dehydrogenation in a fluidized bed without diluting the propane.

According to the invention, it is possible, for example, to operate two fluidized beds in parallel, of which one may be in the state of regeneration from time to time without negative effects on the overall process. The active composition used is chromium oxide or aluminum oxide. The working pressure is typically from 1 to 2 atm and the dehydrogenation temperature is generally from 550 to 600° C. The heat required for the dehydrogenation is introduced into the reaction system by preheating the dehydrogenation catalyst to the reaction temperature. The abovementioned dehydrogenation method is known in the literature as the Snamprogetti-Yarsintez process.

Alternatively to the procedures described above, the heterogeneously catalyzed propane dehydrogenation may also be realized with substantial exclusion of oxygen by a process developed by ABB Lummus Crest (see Proceedings De Witt, Petrochem. Review, Houston, Tex., 1992, P1).

Common to the heterogeneously catalyzed dehydrogenation processes of propane with substantial exclusion of oxygen described hitherto is that they are operated at propane conversions of $\geq 30$ mol % (generally $\leq 60$ mol %) (based on single reaction zone pass). It is advantageous according to the invention that it is sufficient to achieve a propane conversion of from $\geq 5$ mol % to $\leq 30$ mol % or $\leq 25$ mol %. This means that the heterogeneously catalyzed propane dehydrogenation may also be operated at propane conversions of from 10 to 20 mol % (the conversions are based on single reaction zone pass). Among other factors, this is based on the remaining amount of unconverted propane functioning substantially as an inert diluent gas in the subsequent at least one partial zone and later being recycled substantially without loss into the dehydrogenation zone and/or into the at least one partial zone.

For the realization of the abovementioned propane conversions, it is advantageous to carry out the heterogeneously catalyzed propane dehydrogenation at a working pressure of from 0.3 to 3 atm. It is further advantageous to dilute the propane to be dehydrogenated under heterogeneous catalysis with hydrogen. For instance, the heat capacity of the water on the one hand enables a portion of the effect of the endothermicity of the dehydrogenation to be compensated for and, on the other hand, the dilution with steam reduces the reactant and product partial pressure which has a beneficial effect on the equilibrium location of the dehydrogenation. The use of steam, as already mentioned, also has an advantageous effect on the on-stream time of noble metal-containing dehydrogenation catalysts. If required, molecular hydrogen may also be added as a further constituent. The molar ratio of molecular hydrogen to propane is generally $\leq 5$. The molar ratio of hydrogen to propane at a comparative low propane conversion may therefore be from $\geq 0$ to 30, advantageously from 0.1 to 2 and favorably from 0.5 to 1. It also proves to be advantageous for a procedure with low propane conversion that only a comparatively small amount of heat is consumed on single reactor pass of the reaction gas and that comparatively low reaction temperatures are sufficient for achieving the conversion on single ractor pass.

It may therefore be advantageous to carry out the propane dehydrogenation with comparatively low propane conversion (virtually) adiabatically. This means that the starting reaction gas mixture will generally initially be heated to a temperature of from 500 to 700° C. (or from 550 to 650° C.) (for example by direct firing of the wall surrounding it). Normally, a single adiabatic pass through a catalyst bed will then be sufficient in order to achieve the desired conversion, and the reaction gas mixture will cool by from about 30° C. to 200° C. (depending on conversion and dilution). The presence of steam as a heat carrier is also noticeably advantageous from the point of view of an adiabatic method. The lower reaction temperature allows longer on-stream times of the catalyst bed used.

In principle, the heterogeneously catalyzed propane dehydrogenation with comparatively low propane conversion, whether conducted adiabatically or isothermally, can be carried out either in a fixed bed reactor or else in a moving bed or fluidized bed reactor.

Remarkably, to realize the process according to the invention, especially in adiabatic operation, a single shaft furnace reactor which is flowed through by the reaction gas mixture axially and/or radially is sufficient as a fixed bed reactor.

In the simplest case, this is a single closed reaction volume, for example a vessel, whose internal diameter is from 0.1 to 10 m, possibly also from 0.5 to 5 m, and in which the fixed catalyst bed is applied to a support device (for example a grid). The reaction volume which is charged with catalyst and heat-insulated in adiabatic operation is flowed through axially by the hot, propane-containing reaction gas. The catalyst geometry may be either spherical or else annular or strand-shaped. Since the reaction volume can be realized in this case by a very inexpensive apparatus, preference is given to all catalyst geometries which have a particularly low pressure drop. These are in particular catalyst geometries which lead to a large cavity volume or are structured, for example monoliths or honeycombs. To realize a radial flow of the propane-containing reaction gas, the reactor may, for example, consist of two concentric cylindrical grids disposed in a shell and the catalyst bed may be arranged in the annular gap. In the adiabatic case, the metal shell would in turn be thermally insulated.

Useful catalyst charges for a heterogeneously catalyzed propane dehydrogenation with comparatively low propane conversion on a single pass are in particular the catalysts disclosed in DE-A 199 37 107, in particular all of those disclosed by way of example.

After a prolonged operating time, the abovementioned catalysts can be regenerated in a simple manner, for example, by initially passing air (preferably) diluted with nitrogen and/or steam in first regeneration stages over the catalyst bed at an entrance temperature of from 300 to 600° C., frequently from 400 to 550° C. The gas hourly space velocity of regeneration gas may be, for example, from 50 to 10000 $h^{-1}$ and the oxygen content of regeneration gas may be from 0.5 to 20% by volume.

In subsequent further regeneration stages, the regenerating gas used under otherwise identical regeneration conditions may be air. From an application point of view, it is advantageous to flush the catalyst with inert gas (for example $N_2$) before its regeneration.

It is generally to be recommended to subsequently regenerate with pure molecular hydrogen or with molecular hydrogen diluted with inert gas (preferably steam) (the hydrogen content should be 23% by volume) under otherwise identical conditions.

The heterogeneously catalyzed propane dehydrogenation with comparatively low propane conversion ($\leq 30$ mol %) may in all cases be carried out at the same gas hourly space velocities (with regard both to the reaction gas overall and to the propane contained in it) as the variants with high propane conversion (>30 mol %). This gas hourly space velocity of reaction gas may be, for example, from 100 to 10000 $h^{-1}$, frequently from 300 to 5000 $h^{-1}$, i.e. in many cases from about 500 to 3000 $h^{-1}$.

In a particularly elegant manner, the heterogeneously catalyzed propane dehydrogenation with comparatively low propane conversion can be realized in a tray reactor.

This comprises more than one catalyst bed catalyzing the dehydrogenation in spatial succession. The catalyst bed number may be from 1 to 20, advantageously from 2 to 8, or else from 3 to 6. The catalyst beds are preferably arranged in radial or axial succession. From an application point of view, it is advantageous to use the fixed bed catalyst type in such a tray reactor.

In the simplest case, the fixed catalyst beds in a shaft furnace reactor are arranged axially or in the annular gaps of concentric cylindrical grids. However, it is also possible to arrange the annular gaps in segments above one another and to conduct the gas after passing radially through one segment into the next segment above it or below it.

Advantageously, the reaction gas mixture will be subjected to intermediate heating in the tray reactor on its way from one catalyst bed to the next catalyst bed, for example by passing it over heat exchanger ribs heated by hot gases or by passing it through pipes heated by hot combustion gases.

When the tray reactor is otherwise operated adiabatically, it is sufficient for the desired propane conversions ($\leq 30$ mol %), especially when using the catalysts described in DE-A 199 37 107, especially those of the exemplary embodiments, to conduct the reaction gas mixture into the dehydrogenation reactor preheated to a temperature of from 450 to 550° C. and to keep it within this temperature range inside the tray reactor. This means that the entire propane dehydrogenation can thus be realized at very low temperatures, which is particularly advantageous for the on-stream time of the fixed bed catalyst beds between two regenerations.

It is even more beneficial to carry out the catalytic dehydrogenation autothermally, i.e., for example, to carry out the above-outlined intermediate heating in a direct way (autothermal method). To this end, a limited amount of molecular oxygen is added to the reaction gas mixture either before it flows through the first catalyst bed and/or between the subsequent catalyst beds. Depending on the dehydrogenation catalyst used, a limited combustion of the hydrocarbons contained in the reaction gas mixture, any coke or coke-like compounds already deposited on the catalyst surface and/or hydrogen formed in the course of the heterogeneously catalyzed propane dehydrogenation and/or added to the reaction mixture is thus effected (it may also be advantageous from an application point of view to introduce catalyst beds in the tray.reactor which are charged with catalysts which specifically (selectively) catalyze the combustion of hydrogen (and/or of hydrocarbon) (examples of useful catalysts include those of the documents U.S. Pat. No. 4,788,371, U.S. Pat. No. 4,886,928, U.S. Pat. No. 5,430,209, U.S. Pat. No. 5,530,171, U.S. Pat. No. 5,527,979 and U.S. Pat. No. 5,563,314; for example, such catalyst beds may be accommodated in the tray reactor in alternation to the beds containing dehydrogenation catalysts)). The heat of reaction released thus allows virtually isothermal operation of the heterogeneously catalyzed propane dehydrogenation in a quasi-autothermal manner. As the selected residence time of the reaction gas in the catalyst bed is increased, propane dehydrogenation is thus possible at decreasing or substantially constant temperature, which allows particularly long on-stream times between regenerations.

In general, oxygen feeding as described above should be carried out in such a manner that the oxygen content of the reaction gas mixture, based on the amount of propane and propylene contained therein, is from 0.5 to 30% by volume. Useful oxygen sources include both pure molecular oxygen and oxygen diluted with inert gas, for example CO, $CO_2$, $N_2$ or noble gases, but in particular also air. The resulting combustion gases generally have an additional dilution effect and thus support heterogeneously catalyzed propane dehydrogenation.

The isothermicity of the heterogeneously catalyzed propane dehydrogenation can be further improved by incorporating closed (for example tubular) internals which have advantageously, but not necessarily, been evacuated before filling in the spaces between the catalyst beds in the tray reactor. Such internals may also be placed in each catalyst bed. These internals contain suitable solids or liquids which evaporate or melt above a certain temperature, thereby consuming heat, and, when the temperature falls below this value, condense again and thereby release heat.

Another possible method of heating the starting reaction gas mixture for the heterogeneously catalyzed propane dehydrogenation to the required reaction temperature involves combusting a portion of the propane and/or hydrogen contained therein by means of molecular oxygen (for example over suitable specific combustion catalysts, for example by simply passing over and/or through) and to effect the heating to the desired reaction temperature by means of the heat of combustion released in this anner. The resulting combustion products, such as $CO_2$ and $H_2O$, and also any $N_2$ accompanying the molecular oxygen required for the combustion advantageously constitutes inert diluent gases.

The abovementioned hydrogen combustion can be particularly elegantly realized as described in DE-A 10211275. This is a process for continuously partially dehydrogenating propane in the gas phase under heterogeneous catalysis by
    continuously feeding a reaction gas containing the propane to be dehydrogenated to a reaction zone, conducting the reaction gas in the reaction zone over at least one fixed catalyst bed, over which molecular hydrogen and at least partially propylene are formed by catalytic dehydrogenation, adding at least one molecular oxygen-containing gas to the reaction gas before and/or after entry into the reaction zone, partially oxidizing the molecular oxygen in the molecular hydrogen contained in the reaction gas in the reaction zone to give steam and withdrawing a product gas from the reaction zone which comprises molecular hydrogen, steam, propylene and propane, which comprises dividing the product gas removed from the reaction zone into two portions of identical composition and recycling one of the two portions into the dehydrogenation reaction zone and further using the other portion as gas mixture 1 in accordance with the invention.

This process variant is preferred especially when a cycle gas (which may optionally have been subjected to a secondary component removal (for example $C_4$-hydrocarbons such as butene-1)) comprising propane and optionally propylene and resulting from the at least one partial zone is conducted into the dehydrogenation zone as a further propane source in addition to crude propane. This is true in particular when the cycle gas constitutes the only oxygen source for the hydrogen combustion in this process variant.

The product gas mixture formed in the heterogeneously catalyzed propane dehydrogenation in the process according to the invention generally comprises propane, propene, molecular hydrogen, $N_2$, $H_2O$, methane, ethane, ethylene, butene-1, other butenes and other $C_4$-hydrocarbons (n-butane, isobutane, butadiene, etc.), CO and $CO_2$. It will generally be at a pressure of from 0.3 to 10 atm and frequently have a temperature of from 400 to 500° C., in advantageous cases from 450 to 500° C.

While EP-A 117 146, DE-A 3 313 573 and U.S. Pat. No. 3,161,670 recommend using the product gas mixture (gas mixture 1) formed in the heterogeneously catalyzed propane dehydrogenation as such for charging the at least one partial zone, it is usually advantageous according to the invention to remove at least a portion of any $C_4$-hydrocarbons (e.g. n-butane, isobutane, butene-1, other butenes, butadiene, etc.) contained therein from the product gas mixture (gas mixture 1) of the oxydehydrogenation and/or dehydrogenation before its further use for charging the at least one partial zone. When gas mixture 1 contains hydrogen, the abovementioned separation may be accompanied by at least a partial removal of the hydrogen or such a hydrogen removal may be carried out in advance.

The latter may be effected, for example, by passing gas mixture 1, optionally after it has been cooled beforehand in an indirect heat exchanger (advantageously, the heat removed is used for heating a feed gas required for the process according to the invention), through a membrane, generally configured as a tube, which is permeable only to the molecular hydrogen. The molecular hydrogen removed in this way may, if required, be partially recycled into the heterogeneously catalyzed dehydrogenation of propane or be fed to another use. For example, it may be combusted in fuel cells.

Alternatively, a partial or complete hydrogen removal may also be carried out by partial condensation, adsorption and/or rectification (preferably under pressure). The partial or complete removal of the molecular hydrogen from the product gas mixture (gas mixture 1) in the process according to the invention may also be carried out by selective (e.g. heterogeneously catalyzed) combustion thereof with molecular oxygen. The water of reaction formed may be removed either partially or completely or left in the gas mixture, since it is capable of functioning as an inert diluent gas in the at least one partial zone. Catalysts suitable in this regard are disclosed, for example, in U.S. Pat. No. 4,788, 371, U.S. Pat. No. 4,886,928, U.S. Pat. No. 5,430,209, U.S. Pat. No. 5,530,171, U.S. Pat. No. 5,527,979 and U.S. Pat. No. 5,563,314.

The selective combustion of the molecular hydrogen may also be effected effectively in situ as early as during the heterogeneously catalyzed dehydrogenation, for example by oxidation by means of at least one reducible metal oxide additionally added to the dehydrogenation catalyst, as described, for example, in EP-A 832056.

Advantageously, according to the invention, at least 10 mol %, or at least 25 mol %, frequently at least 35 mol %, or at least 50 mol %, in many cases at least 75 mol % and often the entirety of the molecular hydrogen formed in the heterogeneously catalyzed dehydrogenation will be removed beforehand and/or simultaneously, before the remaining gas mixture (gas mixture 1') is used for charging the at least one partial zone. If required, any water present may be removed (e.g. condensed out) from gas mixture 1 before its further use in the at least one partial zone. It will be appreciated that, if required, it is also possible to carry out a removal of other constituents of the product gas mixture (gas mixture 1) other than propane and propylene when removing molecular hydrogen and/or $C_4$-hydrocarbons such as butene-1, etc.

An example of a simple means therefor involves contacting (e.g. by simply passing through) preferably cooled (preferably to temperatures of from 10 to 70° C.), gas mixture 1 with a (preferably high-boiling) organic solvent (preferably hydrophobic) in which propane and propylene are preferentially absorbed, for example at a pressure of from 0.1 to 50 atm and a temperature of from 0 to 100° C. Subsequent desorption, rectification and/or stripping with a gas which behaves inertly with regard to the at least one partial zone and/or is required as a reactant in this reaction zone (e.g. air) recovers a mixture of the propane and propylene in purified form which can be used for charging the at least one partial zone (as already mentioned, in the case of stripping with air, the gas mixture 1' generated may be identical to the gas mixture 2, i.e. can be used immediately as such for charging the at least one partial oxidation). Any molecular hydrogen-containing offgas of the absorption may, for example, be subjected again to a membrane separation and then, if required, the hydrogen removed may be used for heterogeneously catalyzed propane dehydrogenation.

However, the $C_3$-hydrocarbons/$C_4$-hydrocarbons separating factor in the abovementioned separating process is comparatively limited and frequently insufficient for the requirements according to the invention.

A preferred alternative to the separating step via absorption described for the purposes according to the invention is therefore frequently a pressure swing adsorption or a pressure rectification.

Useful absorbents for the absorptive removal described above are in principle any absorbents which are capable of absorbing propane and propylene. The absorbent is preferably an organic solvent which is preferably hydrophobic and/or high-boiling. Advantageously, this solvent has a boiling point (at an atmospheric pressure of 1 atm) of at least 120° C., preferably of at least 180° C., more preferably from 200 to 350° C., in particular from 250 to 300° C., with greater preference from 260 to 290° C. Advantageously, the flash point (at an atmospheric pressure of 1 atm) is above 110° C. In general, useful absorbents include relatively nonpolar organic solvents, for example aliphatic hydrocarbons, which preferably have no externally active polar groups, and also aromatic hydrocarbons. In general, it is desirable that the absorbent has a very high boiling point and at the same time very high solubility for propane and propylene. Examples of useful absorbents include aliphatic hydrocarbons, for example $C_8$-$C_{20}$-alkanes or -alkenes, or aromatic hydrocarbons, for example middle oil fractions from paraffin distillation, or ethers having bulky (sterically demanding) groups on the oxygen atom, or mixtures thereof, to which a polar solvent, for example the 1,2-dimethyl phthalate disclosed in DE-A 43 08 087, may be added. Further suitable absorbents include esters of benzoic acid and phthalic acid with straight-chain alkanols containing from 1 to 8 carbon atoms, such as n-butyl benzoate, methyl benzoate, ethyl benzoate, dimethyl phthalate and diethyl phthalate, and also heat carrier oils such as diphenyl, diphenyl ether and mixtures of diphenyl and diphenyl ether or chlorine derivatives thereof, and triarylalkenes, for example 4-methyl-4'-benzyldiphenylmethane and its isomers 2-methyl-2'-benzyldiphenylmethane, 2-methyl-4'-benzyldiphenylmethane and 4-methyl-2'-benzyldiphenylmethane and mixtures of such isomers. A useful absorbent is a solvent mixture of diphenyl and diphenyl ether, preferably in the azeotropic composition, in particular of about 25% by weight of diphenyl (biphenyl) and about 75% by weight of diphenyl ether, for example the commercially obtainable Diphyl ® (for example obtained from Bayer Aktiengesellschaft). Frequently, this solvent mixture comprises a solvent such as dimethyl phthalate in an amount of from 0.1 to 25% by weight, based on the entire solvent mixture. Particularly useful absorbents also include octanes, nonanes, decanes, undecanes, dodecanes, tridecanes, tetradecanes, pentadecanes, hiexadecanes, heptadecanes and octadecanes, and tetradecanes in particular have proven particularly useful. It is advantageous when the absorbent used on the one hand attains the abovementioned boiling point and on the other hand at the same time does not have too high a molecular weight. Advantageously, the molecular weight of the absorbent is $\leq 300$ g/mol. The paraffin oils having from 8 to 6 carbon atoms described in DE-A 33 13 573 are likewise suitable. Examples of useful trade products include the products sold by Haltermann including Halpasols i, for example Halpasol 250/340 i and Halpasol 250/275 i, and also printing ink distillates sold as PKWF and Printosol. Preference is given to aromatic-free trade products, e.g. those of the PKWFaf type.

The performance of the absorption is subject to no particular restrictions. All processes and conditions familiar to those skilled in the art may be used. Preference is given to contacting the gas mixture with the absorbent at a pressure of from 1 to 50 bar, preferably from 2 to 20 bar, more preferably from 5 to 10 bar, and a temperature of from 0 to 100° C., in particular from 30 to 50° C. The absorption may be carried out either in columns or else in quenching apparatus. It is possible to work in cocurrent or in countercurrent. Examples of useful absorption columns include tray columns (having bubble-cap and/or sieve trays), columns having structured packings (for example sheet metal packings having a specific surface area of from 100 to 1000 $m^2/m^3$, or to 750 $m^2/m^3$, for example Mellapak ® 250 Y) and randomly packed columns (for example packed with Raschig random packings). It is also possible to use trickle and spray towers, graphite block absorbers, surface absorbers such as thick film and thin film absorbers and also plate scrubbers, cross-spray scrubbers and rotary scrubbers. It may also be advantageous to carry out the absorption in a bubble column with or without internals.

The propane and/or propylene may be removed from the absorbent by stripping, decompression-evaporation (flashing) and/or distillation.

The propane and propylene are preferably removed from the absorbent by stripping and/or desorption. The desorption may be carried out in a customary manner by a pressure and/or temperature change, preferably at a pressure of from 0.1 to 10 bar, in particular from 1 to 5 bar, more preferably from 1 to 3 bar, and a temperature of from 0 to 200° C., in particular from 20 to 100° C., more preferably from 30 to 70° C., particularly preferably from 40 to 60° C. An example of a gas suitable for stripping is steam, although preference is given in particular to oxygen/nitrogen mixtures, for example air. When air or oxygen/nitrogen mixtures in which the oxygen content is above 10% by volume are used, it may be sensible to add a gas before or during the stripping process which reduces the explosion range. Particularly suitable gases therefor have a specific heat capacity of $\geq 29$ J/mol·K at 20° C., for example methane, ethane, propane, propene, benzene, methanol, ethanol, and also ammonia, carbon dioxide and water. However, $C_4$-hydrocarbons are to be avoided as such additives according to the invention. Particularly suitable apparatus for the stripping also includes bubble columns with and without internals.

The propane and propylene may also be removed from the absorbent by a distillation or rectification, and the columns used may be those familiar to those skilled in the art and have structured packings, random packings or appropriate internals. Preferred conditions in the distillation or rectification are a pressure of from 0.01 to 5 bar, in particular from 0.1 to 4 bar, more preferably from 1 to 3 bar, and a temperature (in the bottom) of from 50 to 300° C., in particular from 150 to 250° C.

Before it is used for charging the at least one partial zone, a gas mixture 1' obtained by stripping from the absorbent may be fed to another process stage, in order, for example, to reduce the losses of concomitantly stripped absorbent (for example separation in demisters and/or deep filters) and at the same time to protect the at least one partial zone from absorbent, or in order to further improve the separating action between $C_3$-/$C_4$-hydrocarbons. Such a removal of the absorbent may be effected by any of the process steps known to those skilled in the art. An example of a preferred embodiment of such a removal for the purposes of the process according to the invention is the quenching of the starting stream from the stripping apparatus with water. In this case, the absorbent is washed out of this laden starting stream with water and the starting stream is at the same time laden with water. This washing or the quenching, may be effected, for example, at the top of a desorption column using a liquid collecting tray by counterspraying of water or in its own apparatus.

To support the separating effect, internals increasing the quenching surface area may be installed in the quenching space, as known to those skilled in the art from rectifications, absorptions and desorptions.

Water is a preferred washing medium inasfar as it does not normally interfere in the subsequent at least one partial zone. After the water has washed the absorbent out of the propane- and propylene-laden starting stream, the water/absorbent mixture may be fed to a phase separation and the treated starting stream may be fed to the partial zone as a gas mixture 1'.

Both the absorbent stripped to free it of $C_3$ and the absorbent recovered in the phase separation may be reused for the absorption.

The gas mixture 1 and/or the gas mixture 1' generated from it may then be used in a manner known per se in at least one further reaction zone for charging a heterogeneously catalyzed gas phase oxidation and/or ammoxidation of propylene to acrolein and/or acrylic acid and/or acrylonitrile with a charging gas mixture 2. The oxidizing agent used may be pure molecular oxygen, air, oxygen-enriched air or any other mixture of oxygen and inert gas. When the partial oxidation is the conversion of propylene to propylene oxide, the procedure may be, for example, as described in EP-A 372972.

When the partial oxidation is a partial ammoxidation to acrylonitrile, the procedure may be, for example, that of DE-A 2351151. In the case of a partial oxidation of propylene to acrolein and/or acrylic acid, the composition of the gas mixture 2 while also using gas mixture 1 and/or 1' (it is also possible to use mixtures of both, i.e. removal is effected from one portion but not from another) will be adjusted in such a way in the process according to the invention that the following molar ratios are fulfilled:

propane:propene:$N_2$:$O_2$:$H_2O$:others=from 0.5 to 20:1:from 0.1 to 40:from 0.1 to 10:from 0 to 20:from 0 to 1.

According to the invention, the abovementioned molar ratios are advantageously=from 2 to 10:1:from 0.5 to 20:from 0.5 to 5:from 0.01 to 10:from 0 to 1.

According to the invention, it is also favorable when the abovementioned molar ratios are=from 3 to 6:1:from 1 to 10:from 1 to 3:from 0.1 to 2:from 0 to 0.5.

As already mentioned, the heterogeneously catalyzed gas phase partial oxidation of propylene to acrylic acid with molecular oxygen proceeds in two successive steps along the reaction coordinate, of which the first leads to acrolein and the second from acrolein to acrylic acid.

This reaction sequence in two successive steps offset in time opens up the possibility in a manner known per se of implementing the at least one partial zone of the process according to the invention in this case in two oxidation zones arranged in series, and the oxidic catalyst to be used in each of the two oxidation zones can be optimized. For instance, for the first oxidation zone (propylene→acrolein), preference is generally given to a catalyst based on multimetal oxides containing the element combination Mo—Bi—Fe, whereas, for the second oxidation zone (acrolein→acrylic acid), preference is normally given to catalysts based on multimetal oxides containing the element combination Mo—V.

Corresponding multimetal oxide catalysts for the two oxidation zones have been described many times before and are well known to those skilled in the art. For example, EP-A 253 409 refers on page 5 to appropriate US patents.

Advantageous catalysts for the two oxidation zones are also disclosed by DE-A 4 431 957 and DE-A 4431949. This applies in particular to those of the general formula I in both of the abovementioned documents.

For the first step of the partial oxidation, the heterogeneously catalyzed gas phase partial oxidation or propylene to acrolein, useful catalysts are, as already stated, in principle all multimetal oxide compositions containing Mo, Bi and Fe.

These are in particular the multimetal oxide active compositions of the general formula I of DE-A 19955176, the multimetal oxide active compositions of the general formula I of DE-A 19948523, the multimetal oxide active compositions of the general formula I of DE-A 19948523, the multimetal oxide active compositions of the general formulae I, II and III of DE-A 10101695, the multimetal oxide active compositions of the general formulae I, II and III of DE-A 19948248 and the multimetal oxide active compositions of the general formulae I, II and III of DE-A 19955168, and also the multimetal oxide compositions specified in EP-A 700714.

Further suitable catalysts for this oxidation step are the multimetal oxide catalysts containing Mo, Bi and Fe which are disclosed in the documents DE-A 10046957, DE-A 10063162, DE-C 3338380, DE-A 19902562, EP-A 15565, DE-C 2380765, EP-A 807465, EP-A 279374, DE-A 3300044, EP-A 575897, U.S. Pat. No. 4,438,217, DE-A 19855913, WO 98/24746, DE-A 19746210 (those of the general formula II), JP-A 91/294239, EP-A 293224 and EP-A 700714. This is true in particular for the exemplary embodiments in these documents, and among these particular preference is given to those of EP-A 15565, EP-A 575897, DE-A 19746210 and DE-A 19855913. In this context, particular emphasis is given to a catalyst of Example 1c from EP-A 15565 and also a catalyst to be prepared in a corresponding manner whose active composition, however, has the composition $Mo_{12}Ni_{6.5}Zn_2Fe_2Bi_1P0.0065K_{0.06}O_x \cdot 10SiO_2$. Emphasis is further given to the example having the serial No. 3 from DE-A 19855913 (stoichiometry: $Mo_{12}CO_7Fe_3Bi_{0.6}K_{0.08}Si_{1.6}O_x$) as an unsupported hollow cylinder catalyst of geometry 5 mm×3 mm×2 mm (external diameter x height x internal diameter) and also to the multimetal oxide II unsupported catalyst of Example 1 of DE-A 19746210. Mention should also be made of the multimetal oxide catalysts of U.S. Pat. No. 4,438,217, in particular when these hollow cylinders have a geometry of 5.5 mm×3 mm×3.5 mm, or 5 mm×2 mm×2 mm, or 5 mm×3 mm×2 mm, or 6 mm×3 mm×3 mm, or 7 mm×3 mm×4 mm (each external diameter x height x internal diameter).

A multiplicity of multimetal oxide active compositions suitable for the step from propylene to acrolein can be encompassed under the general formula IV $$Mo_{12}Bi_aFe_bX_c^1X_d^2X_e^3X_f^4O_n \qquad (IV)$$

where the variables are defined as follows:

$X^1$=nickel and/or cobalt, $X^2$=thallium, an alkali metal and/or an alkaline earth metal, $X^3$=zinc, phosphorus, arsenic, boron, antimony, tin, cerium, lead and/or tungsten, $X^4$=silicon, aluminum, titanium and/or zirconium, a =from 0.5 to 5, b=from 0.01 to 5, preferably from 2 to 4, c=from 0 to 10, preferably from 3 to 10, d=from 0 to 2, preferably from 0.02 to 2, e=from 0 to 8, prefrably from 0 to 5, f=from 0 to 10 and n=a number which is determined by the valency and the frequency of the elements in (IV) other than oxygen.

They are obtainable in a manner known per se (see, for example, DE-A 4023239) and are customarily shaped in undiluted form to spheres, rings or cylinders or else used in the form of coated catalysts, i.e. preshaped inert supports coated with the active composition. It will be appreciated that they may also be used as catalysts in powder form.

In principle, active compositions of the general formula IV may be prepared in a simple manner by obtaining, from suitable sources of their elemental constituents, a very intimate, preferably finely divided dry mixture corresponding to their stoichiometry and calcining it at temperatures of from 350 to 650° C. The calcination may be effected either under inert gas or under an oxidative atmosphere, e.g. air (mixture of inert gas and oxygen), or else under a reducing atmosphere (e.g. mixture of inert gas, $NH_3$, CO and/or $H_2$). The calcination time may be from a few minutes to a few hours and typically decreases with temperature. Useful sources for the elemental constituents of the multimetal oxide compositions IV are those compounds which are already oxides and/or those compounds which can be converted to oxides by heating, at least in the presence of oxygen.

In addition to the oxides, useful starting compounds of this type are in particular halides, nitrates, formates, oxalates, citrates, acetates, carbonates, amine complexes, ammonium salts and/or hydroxides (compounds such as $NH_4OH$, $(NH_4)_2CO_3$, $NH_4NO_3$, $NH_4CHO_2$, $CH_3COOH$, $NH_4CH_3CO_2$ and/or ammonium oxalate, which on subsequent calcining at the latest decompose to compounds which are released in gaseous form and/or decompose, may additionally be incorporated into the intimate dry mixture).

The intimate mixing of the starting compounds for preparing multimetal oxide active compositions IV may be effected in dry or wet form. Where it is effected in dry form, the starting compounds are advantageously used as a finely divided powder and, after mixing and optional compacting, subjected to calcination. However, the intimate mixing is preferably effected in wet form. Customarily, the starting compounds are mixed with each other in the form of an aqueous solution and/or suspension. Particularly intimate dry mixtures are obtained in the mixing process described when the starting materials are exclusively sources of the elemental constituents present in dissolved form. The solvent used is preferably water. The aqueous composition obtained is then dried, and the drying process is preferably effected by spray drying of the aqueous mixture at outlet temperatures of from 100 to 150° C.

The multimetal oxide active compositions of the general formula IV may be used for the step "propylene→acrolein" either in powder form or shaped to certain catalyst geometries, and the shaping may be effected before or after the final calcination. For example, unsupported catalysts may be prepared from the powder form of the active composition or its uncalcined and/or partially calcined precursor composition by compressing to the desired catalyst geometry (for example by tableting or extruding), optionally adding assistants, for example graphite or stearic acid as lubricants and/or shaping assistants, and reinforcing agents such as microfibers of glass, asbestos, silicon carbide or potassium titanate. Examples of suitable unsupported catalyst geometries include solid cylinders or hollow cylinders having an external diameter and a length of from 2 to 10 mm. In the case of the hollow cylinders, a wall thickness of from 1 to 3 mm is advantageous. It will be appreciated that the unsupported catalyst may also have spherical geometry, and the sphere diameter may be from 2 to 10 mm.

A particularly advantageous hollow cylinder geometry is 5 mm×3 mm×2 mm (external diameter×length×internal diameter), especially in the case of unsupported catalysts.

It will be appreciated that the shaping of the pulverulent active composition or its pulverulent precursor composition which has not yet and/or partially been calcined may also be effected by applying to preshaped inert catalyst supports. The coating of the support bodies to prepare the coated catalysts is generally performed in a suitable rotary vessel, as disclosed, for example, in DE-A 2909671, EP-A 293859 or EP-A 714700. To coat the support bodies, the powder composition to be applied is advantageously moistened and dried again after the application, for example by means of hot air. The coating thickness of the powder composition applied to the support body is advantageously selected within the range from 10 to 1000 μm, preferably within the range from 50 to 500 μm and more preferably within the range from 150 to 250 μm.

The support materials used may be customary porous or nonporous aluminum oxides, silicon dioxide, thorium dioxide, zirconium dioxide, silicon carbide or silicates such as magnesium silicate or aluminum silicate. They generally behave substantially inertly with regard to the target reaction underlying the process according to the invention. The support bodies may have a regular or irregular shape, although preference is given to regularly shaped support bodies having a distinct surface roughness, e.g. spheres or hollow cylinders. Supports suitable for use include substantially nonporous, spherical supports having surface roughness and made of steatite having a diameter of from 1 to 8 mm, preferably from 4 to 5 mm. However, other support bodies suitable for use are cylinders whose length is from 2 to 10 mm and whose external diameter is from 4 to 10 mm. Furthermore, in the case of rings which are suitable as support bodies according to the invention, the wall thickness is typically from 1 to 4 mm. Annular support bodies to be used with preference according to the invention have a length of from 2 to 6 mm, an external diameter of from 4 to 8 mm and a wall thickness of from 1 to 2 mm. Support bodies suitable according to the invention are in particular rings of geometry 7 mm×3 mm×4 mm (external diameter x length x internal diameter). It will be appreciated that the fineness of the catalytically active oxide compositions to be applied to the surface of the support body will be adapted to the desired coating thickness (cf. EP-A 714 700).

Multimetal oxide active compositions used for the step from propylene to acrolein are also compositions of the general formula V $$[Y^1_{a'}Y^2_{b'}O_{x'}]_{p'}[Y^3_{c'}Y^4_{d'}Y^5_{e'}Y^6_{f'}Y^7_{g'}Y^2_{h'}O_{y'}]_{q'} \quad (v)$$

where the variables are defined as follows:
$y^1$=only bismuth or bismuth and at least one of the elements tellurium, antimony, tin and copper,
$y^2$=molybdenum or molybdenum and tungsten,
$y^3$=an alkali metal, thallium and/or samarium,
$y^4$=an alkaline earth metal, nickel, cobalt, copper, manganese, zinc, tin, cadmium and/or mercury,
$y^5$=iron or iron and at least one of the elements chromium and cerium,
$y^6$=phosphorus, arsenic, boron and/or antimony,
$y^7$=a rare earth metal, titanium, zirconium, niobium, tantalum, rhenium, ruthenium, rhodium, silver, gold, aluminum, gallium, indium, silicon, germanium, lead, thorium and/or uranium,
a'=from 0.01 to 8,
b'=from 0.1 to 30,
c'=from 0 to 4,
d'=from 0 to 20,
e'=from 0 to 20,
f'=from 0 to 6, g'=from 0 to 15,
h'=from 8 to 16,
x',y'=numbers which are determined by the valency and frequency of the elements other than oxygen in V and
p,q=numbers whose p/q ratio is from 0.1 to 10, comprising three-dimensional regions of the chemical composition $Y^1{}_aY^2{}_bO_x$, which are delimited from the local environment owing to their different composition from their local environment and whose greatest diameter (longest distance between two points present on the surface (interface) of the region and passing through the center of the region) is from 1 nm to 100 µm, frequently from 10 nm to 500 nm or from 1 µm to 50 or 25 µm.

Particularly advantageous multimetal oxide compositions V according to the invention are those where $Y^1$ is only bismuth.

Among these, preference is given in turn to those which correspond to the general formula VI

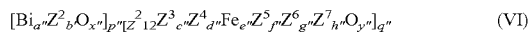   (VI)

where the variants are defined as follows:
$Z^2$=molybdenum or molybdenum and tungsten,
$Z^3$=nickel and/or cobalt,
$Z^4$=thallium, an alkali metal and/or an alkaline earth metal,
$Z^5$=phosphorus, arsenic, boron, antimony, tin, cerium and/or lead,
$Z^6$.=silicon, aluminum, titanium and/or zirconium,
$Z^7$=copper, silver and/or gold,
a"=from 0.1 to 1,
b"=from 0.2 to 2,
c"=from 3 to 10,
d"=from 0.02 to 2,
e"=from 0.01 to 5, preferably 0.1 to 3,
f"=from 0 to 5,
g"=from 0 to 10,
h"=from 0 to 1,
x",y"=numbers which are determined by the valency and frequency of the element other than oxygen in VI,
p",q"=numbers whose p"/q" ratio is from 0.1 to 5, preferably from 0.5 to 2, where very particular preference is given to those compositions VI where $Z^2{}_{b"}$=(tungsten)$_{b"}$ and $Z^2{}_{12}$=(molybdenum)$_{12}$.

It is also advantageous when at least 25 mol % (preferably at least 50 mol % and more preferably at least 100 mol %) of the total proportion of $[Y^1{}_a, Y^2{}_b, O_x,]_p$ ($[Bi_{a"}Z^2{}_{b"}O_{x"}]_{p"}$) of the multimetal oxide compositions V (multimetal oxide compositions VI) suitable according to the invention are present in the multimetal oxide compositions V (multimetal oxide compositions VI) in the form of three-dimensional regions of chemical composition $Y^1{}_a, Y^2{}_b, O_x, [Bi_{a"}Z^2{}_{b"}O_{x"}]$ which are delimited from their local environment owing to their different chemical composition from their local environment and whose greatest diameter is in the range from 1 nm to 100 µm.

With regard to the shaping, the same applies with regard to multimetal oxide composition V catalysts as was stated for the multimetal oxide composition IV catalysts.

The preparation of multimetal oxide composition V active compositions is described, for example, in EP-A 575897 and also in DE-A 19855913.

Among other materials, the inert support materials recommended above are also useful inert materials for diluting and/or delimiting the appropriate fixed catalyst beds, or as the upstream bed which protects them and/or heats the gas mixture.

At this point, it is pointed out that all catalysts and multimetal oxide compositions which have been recommended as suitable for the step from propylene to acrolein are in principle also suitable for the partial ammoxidation of propylene to acrylonitrile.

For the second step, the heterogeneously catalyzed gas phase partial oxidation of acrolein to acrylic acid, useful active compositions are in principle, as already stated, all multimetal oxide compositions containing Mo and V, e.g. those of DE-A 10046928.

A multiplicity of these, for example those of DE-A 19815281, can be encompassed by the general formula VII

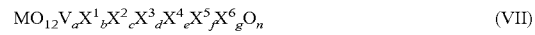   (VII)

where the variables are defined as follows:
$X^1$=W, Nb, Ta, Cr and/or Ce,
$X^2$=Cu, Ni, Co, Fe, Mn and/or Zn,
$X^3$=Sb and/or Bi,
$X^4$=one or more alkali metals,
$X^5$=one or more alkaline earth metals,
$X^6$=Si, Al, Ti and/or Zr,
a=from 1 to 6,
b=from 0.2 to 4,
c=from 0.5 to 18,
d=from 0 to 40,
e=from 0 to 2,
f=from 0 to 4,
g=from 0 to 40 and
n=a number which is determined by the valency and frequency of the elements in VII other than oxygen.

Embodiments preferred according to the invention within the active multimetal oxides VII are those which are embraced by the following definitions of the variables of the general formula VII:
$X^1$=W, Nb, and/or Cr,
$X^2$=Cu, Ni, Co, and/or Fe,
$X^3$=Sb,
$X^4$=Na and/or K,
$X^5$=Ca, Sr and/or Ba,
$X^6$=Si, Al, and/or Ti,
a =from 1.5 to 5,
b=from 0.5 to 2,
c=from 0.5 to 3,
d=from 0 to 2,
e=from 0 to 0.2,
f=from 0 to 1 and
n=a number which is determined by the valency and frequency of the elements other than oxygen in VII.

However, multimetal oxides VII which are very particularly preferred according to the invention are those of the general formula VIII

   (VIII)

where
$Y^1$=w and/or Nb,
$Y^2$=Cu and/or N1,
$Y^5$=Ca and/or Sr,
$y^6$=Si and/or Al,
a'=from 2 to 4,
b'=from 1 to 1.5,
c'=from 1 to 3,
f'=from 0 to 0.5
g'=from 0 to 8 and
n'=a number which is determined by the valency and frequency of the elements other than oxygen in VIII.

The multimetal oxide active compositions (VII) suitable according to the invention are obtainable in a manner known per se, for example as disclosed in DE-A 4335973 or in EP-A 714700.

In principle, multimetal oxide active compositions suitable for the step "acrolein→acrylic acid", especially those of the general formula VII, may be prepared in a simple manner by obtaining, from suitable sources of their elemental constituents, a very intimate, preferably finely divided dry mixture corresponding to their stoichiometry and calcining it at temperatures of from 350 to 600° C. The calcination may be effected either under inert gas or under an oxidative atmosphere, e.g. air (mixture of inert gas and oxygen), or else under a reducing atmosphere (e.g. mixtures of inert gas and reducing gases such as $H_2$, $NH_3$, CO, methane and/or acrolein or the reducing gases mentioned themselves). The calcination time may be from a few minutes to a few hours and typically decreases with temperature. Useful sources for the elemental constituents of the multimetal oxide compositions VII are those compounds which are already oxides and/or those compounds which can be converted to oxides by heating, at least in the presence of oxygen.

The intimate mixing of the starting compounds for preparing multimetal oxide compositions VII may be effected in dry or wet form. Where it is effected in dry form, the starting compounds are advantageously used as a finely divided powder and, after mixing and optional compacting, subjected to calcination. However, the intimate mixing is preferably effected in wet form.

Customarily, the starting compounds are mixed with each other in the form of an aqueous solution and/or suspension. Particularly intimate dry mixtures are obtained in the mixing process described when the starting materials are exclusively sources of the elemental constituents present in dissolved form. The solvent used is preferably water. The aqueous composition obtained is then dried, and the drying process is preferably effected by spray drying of the aqueous mixture at outlet temperatures of from 100 to 150° C.

The resulting multimetal oxide compositions, especially those of the general formula VII, may be used for the acrolein oxidation either in powder form or shaped to certain catalyst geometries, and the shaping may be effected before or after the final calcination. For example, unsupported catalysts may be prepared from the powder form of the active composition or its uncalcined precursor composition by compressing to the desired catalyst geometry (for example by tableting or extruding), optionally adding assistants, for example graphite or stearic acid as lubricants and/or shaping assistants, and reinforcing agents such as microfibers of glass, asbestos, silicon carbide or potassium titanate. Examples of suitable unsupported catalyst geometries include solid cylinders or hollow cylinders having an external diameter and a length of from 2 to 10 mm. In the case of the hollow cylinders, a wall thickness of from 1 to 3 mm is advantageous. It will be appreciated that the unsupported catalyst may also have spherical geometry, and the sphere diameter may be from 2 to 10 mm.

It will be appreciated that the shaping of the pulverulent active composition or its pulverulent precursor composition which has not yet been calcined may also be effected by applying to preshaped inert catalyst supports. The coating of the support bodies to prepare the coated catalysts is generally performed in a suitable rotary vessel, as disclosed, for example, in DE-A 2909671, EP-A 293859 or EP-A 714700.

To coat the support bodies, the powder composition to be applied is advantageously moistened and dried again after the application, for example by means of hot air. The coating thickness of the powder composition applied to the support body is advantageously selected within the range from 10 to 1000 um, preferably within the range from 50 to 500 μm and more preferably within the range from 150 to 250 μm.

The support materials used may be customary porous or nonporous aluminum oxides, silicon dioxide, thorium dioxide, zirconium dioxide, silicon carbide or silicates such as magnesium silicate or aluminum silicate. The support bodies may have a regular or irregular shape, although preference is given to regularly shaped support bodies having a distinct surface roughness, e.g. spheres or hollow cylinders with a grit layer. Supports suitable for use include substantially nonporous, spherical supports having surface roughness and made of steatite having a diameter of from 1 to 8 mm, preferably from 4 to 5 mm. However, other support bodies suitable for use are cylinders whose length is from 2 to 10 mm and whose external diameter is from 4 to 10 mm. Furthermore, in the case of rings as support bodies, the wall thickness is typically from 1 to 4 mm. Annular support bodies to be used with preference have a length of from 2 to 6 mm, an external diameter of from 4 to 8 mm and a wall thickness of from 1 to 2 mm. Suitable support bodies are in particular rings of geometry 7 mm×3 mm×4 mm (external diameter×length×internal diameter). It will be appreciated that the fineness of the catalytically active oxide compositions to be applied to the surface of the support body will be adapted to the desired coating thickness (cf. EP-A 714 700).

Advantageous multimetal oxide active compositions to be used for the step "acrolein→acrylic acid" are also compositions of the general formula IX, $$[D]_p[E]_q \qquad (IX)$$

where the variables are defined as follows:
$D=Mo_{12}V_{a''}Z^1_{b''}Z^2_{c''}Z^3_{d''}Z^4_{e''}Z^5_{f''}Z^6_{g''}O_{x''}$ 
$E:=Z^7_{12}Cu_{h''}H_{i''}O_{y''}$,
$Z^1$=W, Nb, Ta, Cr and/or Ce,
$Z^2$=Cu, Ni, Co, Fe, Mn and/or Zn,
$Z^3$=Sb and/or B1,
$Z^4$=Li, Na, K, Rb, Cs and/or H
$Z^5$=Mg, Ca, Sr and/or Ba,
$Z^6$=Si, Al, Ti and/or Zr,
$Z^7$=Mo, W, V, Nb and/or Ta, preferably Mo and/or W
a''=from 1 to 8,
b'', =from 0.2 to 5,
c''=from 0 to 23,
d''=from 0 to 50,
e''=from 0 to 2,
f''=from 0 to 5,
g''=from 0 to 50,
h''=from 4 to 30,
i=from 0.0 to 20 and
x'', y''=numbers which are determined by the valency and frequency of the element other than oxygen in 1× and
p,q=numbers other than zero whose p/q ratio is from 160:1 to 1:1, and which are obtainable by initially separately forming a multimetal oxide composition E $$Z^7_{12}Cu_{h''}H_{i}''O_{y''} \qquad (E)$$

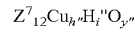

in finely divided form (starting composition 1) and then incorporating the initially formed solid starting composition 1 into an aqueous solution, an aqueous suspension or a finely divided dry mixture of sources of the elements Mo, V, $Z^1$, $Z^2$, $Z^3$, $Z^4$, $Z^5$ and $Z^6$, each of which comprise the aforementioned elements in the stoichiometry D $$MO_{12}V_{a''}Z^1_{b''}Z^2_{c''}Z^3_{d''}Z^4_{e''}Z^5_{f''}Z^6_{g''} \quad (D)$$

(starting composition 2) in the desired p:q ratio, if appropriate drying the resulting aqueous mixture, and calcining the dry precursor mass obtained in this way before or after drying to the desired catalyst geometry at from 250 to 600° C.

Preference is given to multimetal oxide compositions IX where the initially formed solid starting composition 1 is incorporated into an aqueous starting composition 2 at a temperature $\leq 70°$ C. A detailed description of the preparation of multimetal oxide composition VI catalysts is contained, for example, in EP-A 668104, DE-A 19736105, DE-A 10046928, DE-A 19740493 and DE-A 19528646.

With regard to the shaping, the same applies in relation to multimetal oxide IX catalysts as was stated for the multimetal oxide composition VII catalysts.

Multimetal oxide catalysts having outstanding suitability for the step "acrolein→acrylic acid" are also those of DE-A 19815281, especially having multimetal oxide active compositions of the general formula I of this document.

Advantageously, unsupported catalyst rings are used for the step from propylene to acrolein and coated catalyst rings are used for the step acrolein to acrylic acid.

The carrying out of first step of the partial oxidation, from propylene to acrolein, may be carried out using the catalysts described, for example, in a one-zone multiple catalyst tube fixed bed reactor, as described by DE-A 4431957.

The oxidizing agent used is oxygen. When $N_2$ is selected as the inert diluent gas, the use of air as the oxygen source proves to be particularly advantageous.

In general, operation is effected at a propylene : oxygen : inert gases (including steam) volume (1 at STP) ratio of 1:(1.0 to 3.0):(5 to 25), preferably 1:(1.7 to 2.3):(10 to 15). The reaction pressure is typically in the range from 1 to 3 bar and the overall gas hourly space velocity is preferably from 1500 to 4000 l at STP/(l·h). The propylene gas hourly space velocity is typically from 90 to 200 l at STP/(l·h).

The charge gas mixture preferably flows into the one-zone multiple catalyst tube fixed bed reactor from above. The heat exchange medium used is advantageously a salt melt, preferably consisting of 60% by weight of potassium nitrate ($KNO_3$) and 40% by weight of sodium nitrite ($NaNO_2$), or of 53% by weight of potassium nitrate ($KNO_3$), 40% by weight of sodium nitrite ($NaNO_2$) and 7% by weight of sodium nitrate ($NaNO_3$).

Viewed over the reactor, salt melts and reaction gas mixture may be conducted either in cocurrent or in countercurrent. The salt melt itself is preferably conducted around the catalyst tubes in a meandering manner.

When the flow through the catalyst tubes is from top to bottom, it is advantageous to charge the catalyst tubes from bottom to top as follows (when the flow is from bottom to top, the charging sequence is advantageously reversed):

initially to a length of from 40 to 60% of the catalyst tube length either only catalyst, or a mixture of catalyst and inert material, the latter in a proportion by weight of up to 20% by weight, based on the mixture (section C);

next, over a length of from 20 to 40% of the overall tube length, either only catalyst, or a mixture of catalyst and inert material, the latter in a proportion by weight of up to 40% by weight, based on the mixture (section B); and finally, over a length of from 10 to 20% of the overall tube length, a bed of inert material (section A) which is preferably selected in such a way that it causes a very low pressure drop.

Section C is Preferably Undiluted.

The abovementioned charging variant is advantageous in particular when the catalysts used are those of Example 1 of DE-A 10046957 or of Example 3 of DE-A 10046957, and the inert material used is steatite rings of geometry 7 mm×7 mm×4 mm (external diameter x height x internal diameter). With regard to the salt bath temperature, the same applies as is stated in DE-A 4431957.

However, the carrying out of first step of the partial oxidation, from propylene to acrolein, may also be carried out using the catalysts described, for example, in a two-zone multiple catalyst tube fixed bed reactor, as described in DE-A 19910506. In both cases described above, the propene conversion obtained on single pass is normally $\geq 90$ mol %, or $\geq 95$ mol %. The carrying out of second step of the partial oxidation, from acrolein to acrylic acid, may be carried out using the described catalysts, for example, in a one-zone multiple catalyst tube fixed bed reactor, as described in DE-A 4431949. In general, the product mixture of the propylene oxidation to acrolein is conducted as such (optionally after completed intermediate cooling of the same), i.e. without secondary component removal, into the acrolein oxidation to acrylic acid.

The oxygen required for the second step of the partial oxidation is preferably added as air and is generally added directly to the product gas mixture of the propylene oxidation.

In general, the charge gas mixture of such an acrolein oxidation then has the following composition: acrolein : oxygen : steam : inert gas volume ratio (1 at STP) of 1:(1 to 3):(0 to 20):(3 to 30), preferably of 1:(1 to 3):(0.5 to 10):(7 to 18).

The reaction pressure in this case also is generally from 1 to 3 bar and the overall gas hourly space velocity is preferably from 1000 to 3800 l at STP/(l·h). The acrolein gas hourly space velocity is typically from 80 to 190 l at STP/(l·h).

The charge gas mixture preferably likewise flows into the one-zone multiple catalyst tube fixed bed reactor from above. The heat exchange medium used in the second stage is also advantageously a salt melt, preferably consisting of 60% by weight of potassium nitrate ($KNO_3$) and 40% by weight of sodium nitrite ($NaNO_2$), or of 53% by weight of potassium nitrate ($KNO_3$), 40% by weight of sodium nitrite ($NaNO_2$) and 7% by weight of sodium nitrate ($NaNO_3$). Viewed over the reactor, salt melt and reaction gas mixture may be conducted either in cocurrent or in countercurrent. The salt melt itself is preferably conducted around the catalyst tubes in a meandering manner.

When the flow through the catalyst tubes is from top to bottom, it is advantageous to charge the catalyst tubes from bottom to top as follows:

initially to a length of from 50 to 70% of the catalyst tube length either only catalyst, or a mixture of catalyst and inert material, the latter in a proportion by weight of up to 20% by weight, based on the mixture (section C);

next, over a length of from 20 to 40% of the overall tube length, either only catalyst, or a mixture of catalyst and inert material, the latter in a proportion by weight of up to 40% by weight, based on the mixture (section B); and finally, over a length of from 5 to 20% of the overall tube length, a bed of inert material (section A) which is preferably selected in such a way that it causes a very low pressure drop.

Section C is Preferably Undiluted.

When the flow through the catalyst tubes is from bottom to top, the charging of the catalyst tubes is advantageously reversed.

The abovementioned charging variant is advantageous in particular when the catalysts are those of Preparation Example 5 of DE-A 10046928 or those of DE-A 19815281 and the inert material is steatite rings of geometry 7 mm×7 mm×4 mm or 7 mm×7 mm×3 mm (each external diameter× height×internal diameter). With regard to the salt bath temperature, the same applies as was stated in DE-A 44 319 49. It is generally selected in such a way that the acrolein conversion achieved on single pass is normally $\geqq 90$ mol %, or $\geqq 95$ mol %.

However, the carrying out of second step of the partial oxidation, from acrolein to acrylic acid, may also be carried out using the catalysts described, for example, in a two-zone multiple catalyst tube fixed bed reactor, as described in DE-19910508. For the acrolein conversion, that which was specified above applies. In the case that this second step is carried out in a two-zone multiple catalyst tube fixed bed reactor also, the charging gas mixture will advantageously be generated by directly using the product gas mixture of a process directed to the first step of the partial oxidation (optionally after intermediate cooling) (as has been described above). The oxygen required for the second step of the partial oxidation is preferably added as air and, in the second case, added directly to the product gas mixture of the first step of the partial oxidation.

In the case of a two-stage method with immediate reuse of the product gas mixture of the first step of the partial oxidation to charge the second step of the partial oxidation, two one-zone multiple catalyst tube fixed bed reactors or two two-zone multiple catalyst tube fixed bed reactors will generally be connected in series. A mixed connection in series (one-zone/two-zone or vice versa) is also possible.

Between the reactors, an intermediate cooler may be disposed which may optionally comprise inert beds which may perform a filtering function. The salt bath temperature of multiple catalyst tube reactors for the first step of the partial oxidation from propylene to acrylic acid is generally from 300 to 400° C. The salt bath temperature of multiple catalyst tube reactors for the second step of the partial oxidation from propylene to acrylic acid, the partial oxidation of acrolein to acrylic acid, is usually from 200 to 350° C. Also, the heat exchange media (preferably salt melts) are normally conducted through the relevant multiple catalyst tube fixed bed reactors in such amounts that the difference between their entrance and their exit temperatures is generally $\leqq 50 C$. However, as already mentioned, both steps of the partial oxidation of propylene to acrylic acid may also be carried out as described in DE-A 10121592 in a reactor over a charge.

It is mentioned once again that a portion of the charging gas mixture (gas mixture 2) for the first step ("propylene→acrolein") may be cycle gas from the partial oxidation.

This is a gas which remains after target product removal (acrolein and/or acrylic acid removal) from the partial oxidation product gas mixture and is recycled as inert diluent gas into the charge for the first and/or any second step of the partial oxidation from propylene to acrolein and/or acrylic acid.

However, preference is given to recycling such cycle gas containing propane with or without propylene into the charge of the first step of the process according to the invention.

It should also be mentioned that a partial oxidation and/or ammoxidation according to the invention may be carried out in such a way that a reaction gas mixture which contains no oxygen is initially passed over the catalyst charge over the catalyst charge. In this case, the oxygen required for the partial oxidation is provided as lattice oxygen. In a subsequent regeneration step using an oxygen-containing gas (e.g. air, oxygen-enriched air or oxygen-depleted air), the catalyst bed is regenerated, in order to be available again for an oxygen-free reaction gas mixture, and so on.

In summary, a tube bundle reactor within which the catalyst charge along the individual catalyst tubes varies appropriately with the end of the first reaction step (such propylene partial oxidations suitable as reaction zone B according to the invention are taught, for example, by EP-A 911313, EP-A 979813, EP-A 990636 and DE-A 2830765) constitutes the simplest way of realizing two oxidation zones for the two steps of the partial oxidation from propylene to acrylic acid. Optionally, the charge of the catalyst tubes with catalyst is interrupted by an inert bed.

However, preference is given to realizing the two oxidation zones in the form of two tube bundle systems connected in series. These may be disposed in one reactor with the route from one tube bundle to another tube bundle being formed by a bed of inert material (advantageously accessible on foot) not accommodated in a catalyst tube. While the catalyst tubes are generally flowed around by a heat carrier, this does not reach an inert bed configured as described above. Advantageously, the two catalyst tube bundles are therefore accommodated in spatially separate reactors. In general, there is an intermediate cooler between the two tube bundle reactors, in order to reduce any continued acrolein combustion in the product gas mixture which leaves the first oxidation zone. Instead of tube bundle reactors, it is also possible to use plate heat exchanger reactors with salt and/or evaporative cooling, as described, for example, by DE-A 19 929 487 and DE-A 19 952 964.

The reaction temperature in the first oxidation zone is generally from 300 to 450° C., preferably from 320 to 390° C. The reaction temperature in the second oxidation zone is generally from 200 to 300° C., frequently from 220 to 290° C. The reaction pressure in both oxidation zones is expediently from 0.5 to 5 atm, advantageously from 1 to 3 atm. The gas hourly space velocity (1 at STP/l·h) of the oxidation catalysts with reaction gas in both oxidation zones is frequently from 1500 to 2500 $h^{-1}$ or to 4000 $h^{-1}$. The gas hourly space velocity of propylene may be from 100 to 200 l at STP/l·h and more.

In principle, the two oxidation zones in the process according to the invention may be configured as described, for example, in DE-A 19 837 517, DE-A 19 910 506, DE-A 19 910 508 and DE-A 19 837 519. Customarily, the external heating in both oxidation zones, in multizone reactor systems where appropriate, is adapted in a manner known per se to the specific reaction gas mixture composition and also catalyst charge.

The molecular oxygen which is required overall as an oxidizing agent for the at least one partial zone required according to the invention may be added beforehand in its entirety to the charging gas mixture of the at least one partial zone. However, it will be appreciated that it is also possible, for example in the preparation of acrylic acid, to supplement with oxygen after the first partial zone. Preference is given to the latter in acrylic acid preparation.

In the first oxidation zone (propylene→acrolein), preference is given to setting a molar propylene:molecular oxygen ratio of 1:1 to 3, frequently 1:1.5 to 2. Similar numerical values are suitable for the molar acrolein:molecular oxygen ratio in the second oxidation zone (1:0.5 to 1.5 would be preferred) for the partial oxidation of acrolein to acrylic acid.

In both oxidation zones, an excess of molecular oxygen generally has an advantageous effect on the kinetics of the gas phase oxidation. In contrast to the conditions in the dehydrogenation to be used according to the invention, the thermodynamic ratios in the at least one partial oxidation are substantially not influenced by the molar reactant ratio, since the heterogeneously catalyzed gas phase partial oxidation of propylene to acrylic acid is under kinetic control. In principle, it is therefore also possible, for example, to initially charge the propylene in the first oxidation zone in a molar excess over the molecular oxygen. In this case, the excess propylene actually takes on the role of a diluent gas.

However, it is also possible in principle to realize the heterogeneously catalyzed gas phase partial oxidation of propylene to acrylic acid in a single oxidation zone. In this case, both reaction steps are effected in an oxidation reactor which is charged with a catalyst which is able to catalyze the conversions of both reaction steps. It will be appreciated that the catalyst charge may change continuously or abruptly within the oxidation zone along the reaction coordinate. Of course, in one embodiment of the at least one partial oxidation to be used according to the invention in the form of two oxidation zones connected in series, carbon oxide and steam contained in the product gas mixture formed as a by-product in the first oxidation zone and leaving the first oxidation zone may, if required, be partially or completely removed before it is passed on into the second oxidation zone. According to the invention, a procedure will preferably be selected which does not require such a removal.

The source of the molecular oxygen required in the at least one partial oxidation and/or ammoxidation which is admixed with the gas mixture 1 or 1' before its use for charging the partial zone may be either pure molecular oxygen or molecular oxygen diluted with inert gas such as $CO_2$, CO, noble gases, $N_2$ and/or saturated hydrocarbons.

Advantageously, air will be used as the oxygen source for covering at least part of the molecular oxygen requirement.

For the purposes of the present invention, metering in of cold air to the hot gas mixture 1 or 1' may effect cooling of the gas mixture 1 or 1' by a direct route.

In the case of preparation of acrolein and/or acrylic acid, the product gas mixture leaving the partial zone to be used according to the invention is generally composed of the target product acrolein or acrylic acid or its mixture with acrolein, unconverted molecular oxygen, propane, unconverted propylene, molecular nitrogen, steam by-produced and/or used as a diluent gas, carbon oxides by-produced and/or used as a diluent gas, and also small amounts of other lower aldehydes, lower alkanecarboxylic acids (e.g. acetic acid, formic acid and propionic acid) and also maleic anhydride, benzaldehyde, aromatic carboxylic acids and aromatic carboxylic anhydrides (e.g. phthalic anhydride and benzoic acid), possibly further hydrocarbons, e.g. $C_4$-hydrocarbons (e.g. butene-1 and possibly other butenes), and other inert diluent gases.

The target product may be removed from the product gas mixture in a manner known per se (for example by partial condensation of acrylic acid or by absorption of acrylic acid in water or in a high-boiling hydrophobic organic solvent or by absorption of acrolein in water or in aqueous solutions of lower carboxylic acids and subsequent workup of the absorbates; alternatively, the product gas mixture may also be fractionally condensed; cf., for example, EP-A 117146, DE-A 4308087, DE-A 4335172, DE-A 4436243, DE-A 19 924 532 and DE-A 19 924 533). Acrylic acid removal may also be carried out as in EP-A 982287, EP-A 982289, DE-A 19924532, DE-A 10115277, DE-A 19606877, DE-A 19740252, DE-A 19627847, DE-A 10053086 and EP-A 982288.

Unconverted propylene and/or acrolein are optionally likewise removed and recycled into the partial zone.

Preference is given to removing as in FIG. 7 of WO/0196271. Otherwise, the substantial constituents other than acrylic acid and acrolein of the residual gas remaining after the target product removal may, depending on need, crude propane used and dehydrogenation/oxydehydrogenation catalyst used, each be removed separately and/or recycled with the propane as cycle gas (recycle stream) into the charge of the first step of the process according to the invention. However, it will be appreciated that it is also possible to recycle unconverted propane in a mixture with the unconverted propylene alone (as a recycle stream) into 5 this charge. When the process according to the invention is performed continuously, this allows a continuous conversion of propane to acrylic acid and/or acrolein.

The removal of propane and propylene from the residual gas remaining after the target product removal (it generally comprises $O_2$, CO, $CO_2$, $H_2O$, $N_2$, noble gases and also other lower aldehydes, lower alkanecarboxylic acids (e.g. acetic acid, formic acid and propionic acid) and also maleic anhydride, benzaldehyde, aromatic carboxylic acids and aromatic carboxylic anhydrides (e.g. phthalic anhydride and benzoic acid) and hydrocarbons, e.g. $C_4$-hydrocarbons (e.g. butene-1 and any other butenes)) may, as already described, be effected by absorption with subsequent desorption and/or stripping (and also absorbent reuse) in a high-boiling hydrophobic organic solvent. Further separating possibilities are adsorption, rectification, membrane processes and partial condensation. Preference is given to performing the separating processes mentioned at elevated pressure.

When dehydrogenation catalysts are used which are sensitive toward oxygen or oxygen-containing compounds, these oxygenates will be removed from the cycle gas before recycling of cycle gas into the charge of the first step of the process according to the invention. Such an oxygen removal may also be sensible, in order to avoid a total oxidation of the propane in the dehydrogenation stage. The dehydrogenation catalysts of DE-A 19 937 107 are not sensitive toward oxygenates (especially those of Examples 1 to 4 of the DE-A).

As likewise already mentioned, another removal possibility is offered by fractional distillation. Preference is given to carrying out a fractional distillation at low temperatures. The pressure to be applied may be, for example from 10 to 100 bar. The rectification columns used may be randomly packed columns, tray columns or columns having structured packing. Useful tray columns are those having dual-flow trays, bubble-cap trays or valve trays. The reflux ratio may be, for example, from 1 to 10. Examples of other separating possibilities include pressure extraction, pressure swing adsorption, pressure scrubbing, partial condensation and pressure extraction.

It will be appreciated that it is also possible according to the invention to recycle the entire amount of residual gas (as a recycle stream) into the charge of the first step of the process according to the invention, for example when a removal of secondary components (e.g. $C_4$-hydrocarbons (e.g. n-butane, isobutane, butene-1 and possibly other butenes)) is integrated after the first step of the process according to the invention or when the troublesome $C_4$-hydrocarbons do not accumulate (for example 1f they are combusted over suitable catalysts in the partial zone). In this case, the sole outlet for gas constituents other than propane, propylene and molecular oxygen may be disposed between gas mixture 1 and gas mixture 1'.

It will be appreciated that a further outlet may also be installed after the target product removal. If the cycle gas recycled into the propane dehydrogenation comprises carbon monoxide, this may be catalytically combusted to $CO_2$ before the gas is supplemented with fresh crude propane. The heat of reaction released may find use for heating to the dehydrogenation temperature.

Subsequent catalytic combustion of CO contained in the residual gas to $CO_2$ may also be recommended when a removal of the carbon oxides from the residual gas before its recycling as cycle gas into the propane dehydrogenation and/or oxydehydrogenation is desired, and $CO_2$ can be comparatively easily removed (for example by scrubbing with a basic liquid). Such subsequent catalytic Co combustion may also be carried out in the dehydrogenation zone, for example over the above-described dehydrogenation catalysts (e.g. those of DE-A 19937107, in particular those of Ex. 1 to 4).

Another possible procedure is, of course, to recycle a portion of the residual gas unchanged into the propane dehydrogenation and/or oxydehydrogenation and only to remove propane and propylene in a mixture from the remaining portion and likewise recycle them into the propane dehydrogenation and/or oxydehydrogenation and/or into the at least one partial zone. In the latter case, the remaining portion of the residual gas is advantageously combined with the gas mixture 1 or gas mixture 1'.

For the purposes of a fractional distillation of the residual gas, a separating line may be defined, for example, in such a way that, in the rectifying section of the rectification column, substantially all of those components are removed and may be taken off at the top of the column whose boiling point is lower than the boiling point of propylene. These components will primarily be the carbon oxides CO and $CO_2$ and also unconverted oxygen and ethylene and also methane and $N_2$. At the bottom, for example, relatively high-boiling $C_4$-hydrocarbons may be removed.

When a heterogeneously catalyzed oxydehydrogenation of propane is used as the first step of the process according to the invention, it is always still possible to carry out secondary component removals when removals of molecular nitrogen are carried out in the documents DE-A 19837520, DE-A 19837517, DE-A 19837519 and DE-A 19837518.

EXAMPLES

Heterogeneously catalyzed gas phase partial oxidation of propylene in two fixed bed reactors connected in series using different propylene- and propane-containing gas mixtures 2

A) Description of the General Process Conditions

1. First Fixed Bed Reactor for the Step of Partial Oxidation of Propylene to Acrolein

| | |
|---|---|
| Heat-exchange medium used: | Salt melt consisting of 53% by weight of potassium nitrate, 40% by weight of sodium nitrite and 7% by weight of sodium nitrate. |
| Dimensions of the catalyst tube: | total length 4200 mm, internal diameter 26 mm, external diameter 30 mm, wall thickness 2 mm. |
| Reactor: | consists of a jacketed stainless steel cylinder (cylindrical guide tube surrounded by a cylindrical external vessel). The wall thicknesses were always from 2 to 5 mm. The internal diameter of the outer cylinder was 168 mm. The internal diameter of the guide tube was approx. 60 mm. Above and below, the jacketed cylinder was enclosed by a lid and a bottom respectively. The catalyst tube was accommodated in the cylindrical vessel in such a way that it project beyond the lid or bottom at the upper or lower end thereof (sealed) by 250 mm in each case. The heat exchange medium was enclosed in the cylindrical vessel. In order to ensure very uniform thermal boundary conditions at the external wall of the catalyst tube over the entire catalyst tube length disposed in the cylindrical vessel (3700 mm), the heat exchange medium was circulated by bubbling in nitrogen in the cylindrical vessel. The rising nitrogen conveyed the heat exchange medium from bottom to top in the cylindrical guide tube, in order to flow back downward in the intermediate space between cylindrical guide tube and cylindrical external vessel (equally good circulation may also be achieved by circulation by pumping (e.g. propeller pumps)). Electrical heating mounted on the outer jacket allowed the temperature of the heat exhange medium to be controlled at the desired level. There was also air cooling. |
| Reactor charge: | Viewed over the reactor, salt melt and reaction gas mixture (the gas mixture 2 in each case) were conducted in countercurrent. The reaction gas mixture entered the reactor from above. It was conducted into the reaction tube in each case at a temperature of 250° C. The salt melt entered the cylindrical guide tube from below at a temperature $T^{in}$ and left the cylindrical guide tube above at a temperature $T^{out}$. The difference between $T^{in}$ and $T^{out}$ was about 2° C. $T^{ave} = (T^{in} + T^{out})/2$. |
| Catalyst tube charge: (from top to bottom) | Section A: length 50 cm initial bed of steatite rings of geometry 7 mm × 7 mm × 4 mm (external diameter × length × internal diameter). Section B: length 100 cm Catalyst tube charge with a homogeneous mixture of 30% by weight of steatite rings of geometry 5 mm × 3 mm × 2 mm (external diameter × length × internal diameter) and 70% by weight of unsupported catalyst from section C. Section C: length 170 cm Catalyst charge with annular (5 mm × 3 mm × 2 mm = external diameter × length × internal diameter) unsupported catalyst of Example 1 of DE-A 10046957. Section D: length 50 cm final bed of steatite rings of geometry 7 mm × 7 mm × 4 mm (external diameter × length × internal diameter). |
| Loading of the reactor with reaction gas mixture: | in all cases, 3860 g/h of gas mixture 2. |
| Propylene gas hourly space velocity of the catalyst charge: | 100 liters at STP/l · h. |

2. Description of the Intermediate Cooling and Oxygen Intermediate Feeding

The product gas mixture leaving the first fixed bed reactor was conducted for the purposes of intermediate cooling (indirectly by means of air) through a connecting tube (length=400 mm, internal diameter=26 mm, wall thickness=2 mm, material=stainless steel) which was accommodated at a length of 200 mm and centered, charged with an inert bed of steatite spheres of diameter 6 mm and flanged directly to the catalyst tube of the first fixed bed reactor.

In all cases, the gas mixture entered the connecting tube at a temperature of more than 310° C. and left it at a temperature of about 140° C. The gas mixture was then admixed with 290 liters at 40 STP/h of compressed air as the oxygen source.

The resulting charging gas mixture was fed at a temperature of 220° C. to the fixed bed reactor for the step of partial oxidation of acrolein to acrylic acid.

3. Second Fixed Bed Reactor for the Step of Partial Oxidation of Acrolein to Acrylic Acid A fixed bed reactor was used which was identical to that of the first step. Salt melt and reaction gas mixture were conducted in cocurrent viewed over the reactor. The salt melt entered from below, the reaction gas mixture likewise.

The catalyst tube charge (from bottom to top) was:

Section A: length 20 cm
initial bed of steatite rings of geometry 7 mm×7 mm×4 mm (external diameter×length×internal diameter).

Section B: length 100 cm
Catalyst charge with a homogeneous mixture of 30% by weight of steatite rings of geometry 7 mm×3 mm×4 mm (external diameter×length×internal diameter) and 70% by weight of coated catalyst from section C.

Section C: length 200 cm
Catalyst charge with annular (7 mm×3 mm×4 mm=external diameter x length x internal diameter) coated catalyst of Preparation Example 5 of DE-A 10046928.

Section D: length 50 cm
final bed of steatite rings of geometry 7 mm×7 mm×4 mm (external diameter×length×internal diameter).

In all cases, the second reactor was nominally loaded with approx. 4240 g/h of charging gas mixture. Tave is as defined for the first fixed bed reactor.

In all the examples which follow, the propylene conversion in the first reactor was set to 97.7 mol % and the acrolein conversion in the second reactor was set to 99.3 mol %.

The $T^{ave}$ required depending on the composition of the gas mixture 2, and also the yields $Y^{AA}$ (mol %) of acrylic acid which are achieved depending on the composition of gas mixture 2, based on ropylene converted over both reactors, and selectivities of carbon oxide formation $S^{CO_x}$ (mol %) in the individual examples have the values which follow.

B) Example 1

The composition of gas mixture 2 was:
6.18% by volume of propylene,
33.1% by volume of propane,
12.3% by volume of oxygen,
0.15% by volume of $CO_x$,
46.7% by volume of $N_2$, and
1.63% by volume of $H_2O$.
$Y^{AA}$=86.1 mol % $T^{ave}$ 1$^{st}$ reactor=316° C.
$S^{CO_x}$=9.2 mol % $T^{ave}$ 2$^{nd}$ reactor=274° C.

C) Example 2

The composition of gas mixture 2 was:
6.04% by volume of propylene,
42.3% by volume of propane,
10.4% by volume of oxygen,
0.15% by volume of $CO_x$,
39.5% by volume of $N_2$, and
1.60% by volume of $H_2O$.
$Y^{AA}$=85.2 mol % $T^{ave}$ 1$^{st}$ reactor=322° C.
$S^{CO_x}$=9.9 mol % $T^{ave}$ 2$^{nd}$ reactor=278° C.

D) Example 3

The composition of gas mixture 2 was:
0.20% by volume of ethane,
6.14% by volume of propylene,
33.0% by volume of propane,
12.2% by volume of oxygen,
0.16% by volume of $CO_x$,
46.6% by volume of $N_2$, and
1.65% by volume of $H_2O$.
$Y^{AA}$=86.1 mol % $T^{ave}$ 1$^{st}$ reactor =316° C.
$S^{CO_x}$=9.2 mol % $T^{ave}$ 2$^{nd}$ reactor =274° C.

E) Example 4

The composition of gas mixture 2 was:
0.22% by volume of ethylene,
6.13% by volume of propylene,
33.0% by volume of propane,
12.2% by volume of oxygen,
0.16% by volume of $CO_x$,
46.6% by volume of $N_2$, and
1.64% by volume of $H_2O$.
$Y^{AA}$=86.1 mol % $T^{ave}$ 1$^{st}$ reactor=316° C.
$S^{CO_x}$=9.2 mol % $T^{ave}$ 2$^{nd}$ reactor =274° C.

F) Example 5

The composition of gas mixture 2 was:
0.20% by volume of n-butane,
6.14% by volume of propylene,
33.0% by volume of propane,
12.2% by volume of oxygen,
0.16% by volume of $CO_x$,
46.6% by volume of $N_2$, and
1.65% by volume of $H_2O$.
$Y^{AA}$=85.2 mol % $T^{ave}$ 1$^{st}$ reactor =316.5° C.
$S^{CO_x}$=9.9 mol % $T^{ave}$ 2$^{nd}$ reactor =274° C.

G) Example 6

The composition of gas mixture 2 was:
2.02% by volume of n-butane,
5.98% by volume of propylene,
32.4% by volume of propane,
12.0% by volume of oxygen,
0.16% by volume of $CO_x$,
45.8% by volume of $N_2$, and
1.64% by volume of $H_2O$.

The desired propylene conversion could no longer be maintained by increasing $T^{ave}$ for reasons of catalyst compatibility.

H) Example 7

The composition of gas mixture 2 was:
0.05% by volume of butene-1,
6.16% by volume of propylene,
33.0% by volume of propane,
12.3% by volume of oxygen,
0.16% by volume of $CO_x$,
46.7% by volume of $N_2$, and
1.70% by volume of $H_2O$.
$y^{AA}$ 85.1 mol % $T^{ave}$ $1^{st}$ reactor=318° C.
$S^{CO_x}$=10 mol % $T^{ave}$ $2^{nd}$ reactor=281° C.

I) Example 8

The composition of gas mixture 2 was:
0.09% by volume of butene-1,
6.16% by volume of propylene,
32.9% by volume of propane,
12.3% by volume of oxygen,
0.15% by volume of $CO_x$,
46.8% by volume of $N_2$, and
1.68% by volume of $H_2O$.
$Y^{AA}$=85.0 mol % $T^{ave}$ $1^{st}$ reactor=320° C.
$S^{CO_x}$=10.2 mol % $T^{ave}$ $2^{nd}$ reactor=287° C.

J) Example 9

The composition of gas mixture 2 was:
0.20% by volume of butene-1,
6.19% by volume of propylene,
32.7% by volume of propane,
12.3% by volume of oxygen,
0.18% by volume of $Co_x$,
46.7% by volume of $N_2$, and
1.71% by volume of $H_2O$.

The desired propylene conversion could no longer be maintained by increasing $T^{ave}$ for reasons of catalyst compatibility.

We claim:

1. A process for preparing at least one partial oxidation product of propylene selected from the group consisting of acrolein, acrylic acid and propylene oxide, said process comprising:
    a) subjecting crude propane to at least one reaction selected from the group consisting of a homogeneous dehydrogenation, a heterogeneously catalyzed dehydrogenation, a homogeneous oxydehydrogenation, wherein the reaction(s) is/are carried out under at least one condition selected from the group consisting of 1) in the presence of oxygen and 2) with the exclusion of oxygen, and a heterogeneously catalyzed oxydehydrogenation, to obtain a gas mixture 1 comprising propane and propylene,
    b) optionally removing, converting to by-products, or both removing and converting to by-products, a portion of the constituents other than propane and propylene from all of or a part of the gas mixture 1 to obtain a gas mixture 1' comprising propane, propylene and compounds other than oxygen, propane and propylene, and
    c) subjecting a gas mixture 2 comprising the gas mixture 1, the gas mixture 1', or the gas mixture 1' and the remainder of gas mixture 1, to a heterogeneously catalyzed gas phase partial oxidation of the propylene contained in the gas mixture 1, the gas mixture 1', or the gas mixture 1' and the remainder of gas mixture 1, wherein the total content of $C_4$-hydrocarbons of the gas mixture 2 is ≦3% by volume.

2. The process as claimed in claim 1, wherein the total content of $C_4$-hydrocarbons of the gas mixture 2 is ≦2.5% by volume.

3. The process as claimed in claim 1, wherein the total content of $C_4$-hyclrocarbons of the gas mixture 2 is ≦2.0% by volume.

4. The process as claimed in claim 1, wherein the total content of $C_4$-hydrocarbons of the gas mixture 2 is ≦1.5% by volume.

5. The process as claimed in claim 1, wherein the total content of $C_4$-hydrocarbons of the gas mixture 2 is ≦1.0% by volume.

6. The process as claimed in claim 1, wherein the total content of $C_4$-hydrocarbons of the gas mixture 2 is ≦0.5% by volume.

7. The process as claimed in claim 1, wherein the total content of $C_4$-hydrocarbons of the gas mixture 2 is ≧0.07% by volume.

8. The process as claimed in claim 1, wherein the total content of $C_4$-hydrocarbons of the gas mixture 2 is ≧0.05% by volume.

9. The process as claimed in claim 1, wherein gas mixture 1' comprises 0.1% by volume of compounds other than oxygen, propane and propylene.

10. The process as claimed in claim 1, wherein gas mixture 1' comprises ≧0.2% by volume of compounds other than oxygen, propane and propylene.

11. The process as claimed in claim 1, wherein gas mixture 1' comprises ≧0.3% by volume of compounds other than oxygen, propane and propylene.

12. The process as claimed in claim 1, wherein gas mixture 1' comprises ≧0.5% by volume of compounds other than oxygen, propane and propylene.

13. The process as claimed in claim 1, wherein gas mixture 1' comprises ≧1% by volume of compounds other than oxygen, propane and propylene.

14. The process as claimed in claim 1, wherein gas mixture 1' comprises ≧3% by volume of compounds other than oxygen, propane and propylene.

15. The process as claimed in claim 1, wherein gas mixture 1' comprises ≧5% by volume of compounds other than oxygen, propane and propylene.

16. The process as claimed in claim 1, wherein gas mixture 1' comprises ≧10% by volume of compounds other than oxygen, propane and propylene.

17. The process as claimed in claim 1, wherein gas mixture 1' comprises ≧30% by volume of compounds other than oxygen, propane and propylene.

18. The process as claimed in claim 1, wherein the gas mixture 2 comprises up to 60% by volume of propane.

19. The process as claimed in claim 1, wherein the gas mixture 2 comprises up to 50% by volume of propane.

20. The process as claimed in claim 1, wherein gas mixture 2 comprises from 20 to 40% by volume of propane.

21. The process as claimed in claim 1, wherein the gas mixture 2 has the following contents:
    from 7 to 15% by volume of $O_2$,
    from 5 to 10% by volume of propylene,
    from 15 to 40% by volume of propane,
    from 25 to 60% by volume of nitrogen,
    a sum of from 1 to 5% by volume of CO, $CO_2$ and $H_2O$, and
    from 0 to 5% by weight of other compounds.

22. The process as claimed in claim 1, wherein the gas mixture 2 has the following contents:
$H_2O \leq 60\%$ by volume,
$N_2 \leq 80\%$ by volume,
$O2 > 0, 20\%$ by volume,
$CO \leq 2\%$ by volume,
$CO_2 > 0, 5\%$ by volume,
ethane $\leq 10\%$ by volume,
ethylene $\leq 5\%$ by volume,
methane $\leq 5\%$ by volume,
propane $>0, \leq 50\%$ by volume,
cyclopropane $\leq 0.1\%$ by volume,
propyne $\leq 0.1\%$ by volume,
propadiene $\leq 0.1\%$ by volume,
propylene $>0, \leq 30\%$ by volume,
$H_2 \leq 30\%$ by volume,
isobutane $\leq 3\%$ by volume,
n-butane $\leq 3\%$ by volume,
trans-butene-2 $\leq 1\%$ by volume,
cis-butene-2 $\leq 1\%$ by volume,
butene-1 $\leq 1\%$ by volume,
isobutene $\leq 1\%$ by volume,
butadiene-1,3 $\leq 1\%$ by volume,
butadiene-1,2 $\leq 1\%$ by volume,
butyne-1 $\leq 0.5\%$ by volume, and
butyne-2 $\leq 0.5\%$ by volume.

23. The process as claimed in claim 1, wherein the crude propane comprises $\geq 0.25\%$ by volume of constituents other than propane and propylene.

24. The process as claimed in claim 1, wherein the crude propane comprises $\geq 1\%$ by volume of compounds other than propane and propylene.

25. The process as claimed in claim 1, wherein the crude propane comprises $\geq 2\%$ by volume of compounds other than propane and propylene.

26. The process as claimed in claim 1, wherein the crude propane comprises $\geq 3\%$ by volume of compounds other than propane and propylene.

27. The process as claimed in claim 1, wherein the crude propane comprises up to 6% by volume of $C_4$-hydrocarbons.

28. The process as claimed in claim 1, wherein the crude propane comprises from 0.1 to 6% by volume of $C_4$-hydrocarbons.

29. The process as claimed in claim 1, wherein the crude propane meets the following specifications:
propane content $\geq 90\%$ by volume,
total content of propane and propylene $\leq 99\%$ by volume,
total content of $C_4$-hydrocarbons $\leq 6\%$ by volume,
butene-1 content $\leq 0.5\%$ by volume,
total content of butenes $\leq 0.5\%$ by volume,
ethane content $\leq 10\%$ by volume,
ethylene content $\leq 5\%$ by volume,
methane content $\leq 5\%$ by volume,
cyclopropane content $\leq 0.1\%$ by volume, and
propylene content $\leq 10\%$ byvolume,
wherein the total content of $C_3$-hydrocarbons other than propane and propylene is $\leq 0.3\%$ by volume, and
wherein the total content of $C_5$-hydrocarbons $\leq 0.3\%$ by volume, and total content of $C_6$- to $C_8$-hydrocarbons is $\leq 600$ ppm by volume.

30. The process as claimed in claim 1, wherein the propane conversion in step (a) is from $\geq 5$ mol % to $\leq 30$ mol %.

31. The process as claimed in claim 1, wherein the at least one partial oxidation product of propylene is removed from the product gas mixture of the gas phase partial oxidation and at least unconverted propane present in this product gas mixture is recycled into step (a) and/or into the gas phase partial oxidation.

32. The process as claimed in claim 1, wherein the process is carried out in a reaction zone over a catalyst charge whose active composition is at least one multimetal oxide composition which comprises Mo and V, at least one of Te and Sb, and at least one selected from the group consisting of Nb, Ta, W, Ti, Al, Zr, Cr, Mn, Ga, Fe, Ru, Co, Rh, Ni, Pd, Pt, La, Bi, B, Ce, Sn, Zn, Si, Na, Li, K, Mg, Ag, Au and In, in combination.

33. The process as claimed in claim 32, wherein the active composition is at least one multimetal oxide composition which comprises the elemental stoichiometry I

where
$M^1$=Te and/or Sb,
$M^2$=at least one selected from the group consisting of Nb, Ta, W, Ti, Al, Zr, Cr, Mn, Ga, Fe, Ru, Co, Rh, Ni, Pd, Pt, La, Bi, Ce, Sn, Zn, Si, Na, Li, K, Mg, Ag, Au and In,
b=from 0.01 to 1,
c=from >0 to 1 and
d=from >0 to 1.

34. The process as claimed in claim 33, wherein $M^1$ is Te and $M^2$ is at least one of Nb, Ta, W and Ti.

35. The process as claimed in claim 33, wherein $M^2$ is Nb.

36. The process as claimed in claim 32, wherein the X-ray diffractogram of the at least one multimetal oxide active composition has reflections h and i whose peak locations are at the reflection angles $22.2 \pm 0.5°$ (h) and $27.3 \pm 0.5°$ (i).

37. The process as claimed in claim 36, wherein the X-ray diffractogram additionally has a reflection k whose peak is at $28.2 \pm 0.50°$.

38. The process as claimed in claim 36, wherein the reflection h has the highest intensity within the X-ray diffractogram and a maximum half-height width of 0.5°.

39. The process as claimed in claim 38, wherein the half-height width of the reflection i and of the reflection k are each additionally at the same time $\leq 1°$ and the intensity $P_k$ of the reflection k and the intensity $P_i$ of the reflection i fulfill the condition $0.20 \leq R \leq 0.85$ where R is the intensity ratio defined by the formula $$R = P_i/(P_i + P_k).$$

40. The process as claimed in claim 32, wherein the X-ray diffractogram of the at least one multimetal oxide active composition has no reflection whose maximum is at $2\theta = 50 \pm 0.3°$.

41. The process as claimed in claim 1, wherein step (a) is carried out in a separate reaction zone.

42. The process as claimed in claim 1, wherein step (a) is a heterogeneously catalyzed dehydrogenation.

43. The process as claimed in claim 1, wherein a portion of the constituents other than propane and propylene contained in the gas mixture 1 is removed which comprises at least one $C_4$-hydrocarbon.

44. The process as claimed in claim 41, wherein a the heterogeneously catalyzed gas phase partial oxidation, is carried out with a catalyst having an active composition comprising Mo, Bi and Fe.

45. The process as claimed in claim 41, wherein the heterogeneously catalyzed gas phase partial oxidation is carried out with a catalyst having an active composition of formula IV

where the variables are defined as follows:
$X_1$=nickel and/or cobalt,
$X_2$=thallium, an alkali metal and/or an alkaline earth metal,
$X_3$=zinc, phosphorus, arsenic, boron, antimony, tin, cerium, lead and/or tungsten,
$X_4$=silicon, aluminum, titanium and/or zirconium,
a=from 0 to 5,
b=from 0.01 to 5,
c=from 0 to 10,
d=from 0 to 2,
e=from 0 to 8,
f=from 0 to 10, and
n=a number which is determined by the valency and frequency of the elements in (IV) other than oxygen.

46. The process as claimed in claim 41, wherein the heterogeneously catalyzed gas phase partial oxidation is carried out with a catalyst having an, active composition comprising Mo and V.

47. The process as claimed in claim 41, wherein the heterogeneously catalyzed gas phase partial oxidation is carried out with a catalyst having a multimetal oxide of formula VII $$Mo_{12}V_aX_b^1X_c^2X_d^3X_e^4X_f^5X_g^6O_n, \quad \text{(VII)}$$

where the variables are defined as follows:
$X^1$=W, Nb, Ta, Cr and/or Ce,
$X^2$=Cu, Ni, Co, Fe, Mn and/or Zn,
$X^3$=Sb and/or Bi,
$X^4$=one or more alkali metals,
$X^5$=one or more alkaline earth metals,
$X^6$=Si, Al, Ti and/or Zr,
a=from 1 to 6,
b=from 0.2 to 4,
c=from 0.5 to 18,
d=from 0 to 40,
e=from 0 to 2,
f=from 0 to 4,
g=from 0 to 40, and
n=a number which is determined by the valency and frequency of the elements in VII other than oxygen.

48. The process as claimed in claim 1, wherein crude propane is subjected to a heterogeneously catalyzed dehydrogenation and the gas mixture 1 is subjected to a heterogeneously catalyzed gas phase partial oxidation of propylene present in gas mixture 1.

49. The process as claimed in claim 1, wherein crude propane is subjected and also in the presence of steam to a heterogeneously catalyzed dehydrogenation, and steam is partly or completely removed by condensation from gas mixture 1 formed in step (a) and the resulting gas mixture 1' is subjected to a heterogeneously catalyzed gas phase partial oxidation of propylene present in gas mixture 1'.

50. The process as claimed in claim 1, wherein crude propane is subjected to an autothermal heterogeneously catalyzed dehydrogenation.

51. The process as claimed in claim 1, wherein in advance of said process $C_4$-hydrocarbons are rectificatively removed from the crude propane.

* * * * *